US009777185B2

United States Patent
Gopalan et al.

(10) Patent No.: US 9,777,185 B2
(45) Date of Patent: Oct. 3, 2017

(54) AZLACTONE BASED THERMALLY CROSSLINKABLE POLYMER COATING FOR CONTROLLING CELL BEHAVIOR

(71) Applicant: Wisconsin Alumni Research Foundation, Madison, WI (US)

(72) Inventors: Padma Gopalan, Madison, WI (US); William L. Murphy, Waunakee, WI (US); Samantha Kelly Schmitt, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 89 days.

(21) Appl. No.: 14/658,402

(22) Filed: Mar. 16, 2015

(65) Prior Publication Data

US 2016/0272840 A1 Sep. 22, 2016

(51) Int. Cl.
- C09D 133/14 (2006.01)
- C08F 220/28 (2006.01)
- C12N 5/00 (2006.01)

(52) U.S. Cl.
CPC .......... C09D 133/14 (2013.01); C08F 220/28 (2013.01); C12N 5/0068 (2013.01); C12N 2533/40 (2013.01); C12N 2537/10 (2013.01)

(58) Field of Classification Search
CPC .................................................. C09D 133/14
See application file for complete search history.

(56) References Cited

FOREIGN PATENT DOCUMENTS

WO  WO 02/056021 A2 * 7/2002 .......... C08F 293/005

OTHER PUBLICATIONS

Chemical abstracts registry No. 29513-26-6 for 4,4-dimethyl-2-vinylazlactone, 2002, one page.*
Hansen et al., Microstructured Block Copolymer Surfaces for Control of Microbe Adhesion and Aggregation, Biosensors 4, Mar. 14, 2014, pp. 63-75.
Schmitt et al., Ultrathin coatings on polymer substrates for chemically defined culture of human mesenchymal stem cells, ACS Poster Abstract, Feb. 2015.
Lokitz et al., Manipulating Interfaces through Surface Confinement of Poly(glycidyl methacrylate)-block-poly(vinyldimethylazlactone), a Dually Reactive Block Copolymer, Macromolecules 45, Aug. 9, 2012, pp. 6438-6449.
Schmitt et al., Crosslinked PEG mats for peptide immobilization and stem cell adhesion, J. Mater. Chem B, 1, Jan. 7, 2013, pp. 1349-1360.
Cullen et al., Surface-Anchored Poly(2-vinyl-4,4-dimethyl azlactone) Brushes as Templates for Enzyme Immobilization, Langmuir 24, Oct. 29, 2008, pp. 13701-13709.

(Continued)

Primary Examiner — Megan McCulley
(74) Attorney, Agent, or Firm — Bell & Manning, LLC

(57) ABSTRACT

Random copolymers, crosslinked thin films of the random copolymers and cell culture substrates comprising the crosslinked thin films are provided. Also provided are methods of making and using the copolymers, thin films and substrates. The copolymers are polymerized from glycidyl methacrylate monomers and vinyl azlactone monomers. The crosslinked thin films are substrate independent, in that they need not be covalently bound to a substrate to form a stable film on the substrate surface.

16 Claims, 15 Drawing Sheets

(56) References Cited

OTHER PUBLICATIONS

Pierschbacher et al., Cell attachment activity of fibronectin can be duplicated by small synthetic fragments of the molecule, Nature 309, May 3, 1984, pp. 30-33.
Tocce et al., Functionalization of reactive polymer multilayers with RGD and an antifouling motif: RGD density provides control over human corneal epithelial cell—substrate interactions, Journal of Biomedical Materials Research Part A, 100A, Oct. 4, 2011, pp. 84-93.
Coleman et al., Immobilization of Protein A at high density on azlactone-functional polymeric beads and their use in affinity chromatography, Journal of Chromatography 512, 1990, pp. 345-363.

* cited by examiner

Table 1. Compositions of P(PEGMEMA-r-GMA-r-VDMA)

| Copolymer | Feed Composition | | | Mn | Mw | PDI | Proton NMR Composition | | |
|---|---|---|---|---|---|---|---|---|---|
| | VDM | GMA | PEGMEMA | | | | VDM | GMA | PEGMEMA |
| 1 | 0.16 | 0.07 | 0.77 | 43,094 | 55,192 | 1.28 | 0.24 | 0.11 | 0.65 |
| 2 | 0.15 | 0.04 | 0.81 | 28,144 | 39,189 | 1.39 | 0.17 | 0.10 | 0.73 |
| 3 | 0.1 | 0.07 | 0.83 | 50,841 | 71,940 | 1.41 | 0.145 | 0.12 | 0.74 |
| 4 | 0.07 | 0.07 | 0.86 | 38,575 | 53,040 | 1.37 | 0.125 | 0.11 | 0.76 |

FIG. 4

AZLACTONE BASED THERMALLY CROSSLINKABLE POLYMER COATING FOR CONTROLLING CELL BEHAVIOR

REFERENCE TO GOVERNMENT RIGHTS

This invention was made with government support under 1306482 awarded by the National Science Foundation. The government has certain rights in the invention.

BACKGROUND

Regulation of fundamental stem cell behavior using two-dimensional synthetic templates in vitro is of immense importance in regenerative medicine. In particular, human mesenchymal stem cells (hMSCs) are of great interest due to their ability to undergo multilineage differentiation, and derivation from adult tissues. Control over cell behaviors such as adhesion, proliferation and differentiation is likely to facilitate increased therapeutic applications of stem cells. However, the inherent complexity of the native extracellular microenvironment makes decoupling the cause and effect of particular signaling cues (e.g. proteins, soluble factors, cell-cell interactions) difficult. For a true understanding of the identity and concentration of extracellular matrix fragments (peptides) necessary for even simple stem cell adhesion, the microenvironment needs to be simplified. Although growing cells on a chemically defined surface, where cell-surface interactions are known and quantifiable, is desired, it is rarely achieved. Cells are traditionally grown on tissue culture polystyrene (TCPS), which, like most other materials, undergoes rapid adsorption of proteins in biological fluid, creating a poorly defined interface for cell studies, where identity, density and orientation of the biomolecules is unknown. Hence, a large amount of research has focused on creating synthetic two-dimensional templates for chemically defined cell culture and expansion including self-assembled monolayers (SAMs), hydrogels, polymer brushes, thin films, and layer by layer films. To better regulate cell-template interactions common synthetic templates employ poly(ethylene glycol) (PEG) to provide a "blank slate" background to cells. PEG, when used in combination with specific peptides on synthetic templates, can provide a powerful platform for regulating stem cell behavior.

Polymer coatings are one of the few templates that are compatible with a wide range of substrates and have good physical stability. However, the polymer coating must remain insoluble and not delaminate from the underlying substrate for the duration of the cell culture. This limits the composition of the polymers that can be used.

SUMMARY

Random copolymers, crosslinked thin films of the random copolymers and cell culture substrates comprising the crosslinked thin films are provided. Also provided are methods of making and using the copolymers, thin films and substrates.

One embodiment of a random copolymer is a random copolymer of glycidyl methacrylate and 4,4-dimethyl-2-vinylazlactone comprising the structure:

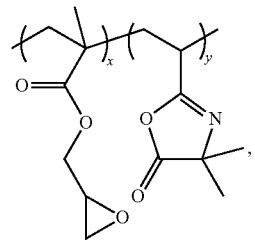

wherein x any y represent the mole fractions of the polymerized glycidyl methacrylate and 4,4-dimethyl-2-vinylazlactone monomers; and the glycidyl groups and the azlactone groups are distributed randomly along the copolymer backbone. In some embodiments, the random copolymer comprises no greater than about 30 mole percent of additional monomer.

Random copolymers of this type can be formed into coatings on a substrate to provide a coated substrate comprising: a substrate having a surface; and a film of crosslinked random copolymers on the surface of the substrate, the crosslinked random copolymers having backbone chains comprising polymerized 4,4-dimethyl-2-vinylazlactone monomers and monomers that provide covalent crosslinks between the backbone chains, the crosslinked random copolymers comprising the structure:

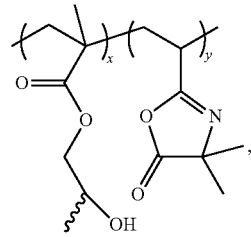

wherein x any y represent the mole fractions of the crosslinked monomer and the 4,4-dimethyl-2-vinylazlactone monomers; ⌇ represents a crosslink to another copolymer backbone chain; and the glycidyl groups, the crosslinks, and the azlactone groups are distributed randomly along the copolymer backbone.

Coated substrates of this type can provide a cell culture substrate comprising: a substrate having a surface; and a film comprising crosslinked random copolymers on the surface of the substrate, the crosslinked random copolymers having backbone chains comprising polymerized monomers comprising covalently linked peptide chains and monomers that provide covalent crosslinks between the backbone chains, the crosslinked random copolymers comprising the structure:

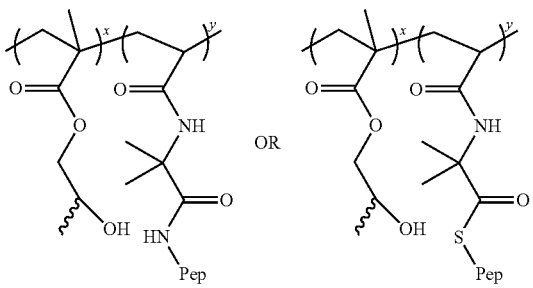

wherein x any y represent the mole fractions of the crosslinked monomers and the monomers comprising covalently linked peptide chains; / represents a crosslink to another copolymer backbone chain; Pep represents a peptide chain; and the crosslinks and peptide chains are distributed randomly along the copolymer backbone.

An embodiment of a cell culture substrate can be made by: copolymerizing about 99 to about 85 mole percent 4,4-dimethyl-2-vinylazlactone monomer and about 1 to about 15 mole percent glycidyl methacrylate monomer to form a random copolymers of 4,4-dimethyl-2-vinylazlactone and glycidyl methacrylate; forming a film of the random copolymers on a surface of a substrate; crosslinking the glycidyl groups on the random copolymers to form a crosslinked random copolymer film; and reacting at least a portion of the azlactone functionalities on the random copolymers with molecules comprising a peptide chain to covalently bind the peptide chains to the random copolymers. At least a portion of the azlactone functionalities may then be reacted with molecules comprising a polyethylene glycol chain to covalently bind the polyethylene glycol chains to the random copolymers.

Another embodiment of a random copolymer is a random copolymer of glycidyl methacrylate, 4,4-dimethyl-2-vinylazlactone and polyethylene glycol methyl ether methacrylate comprising the structure:

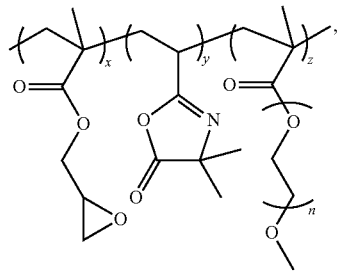

wherein x, y and z represent the mole fractions of the polymerized glycidyl methacrylate, 4,4-dimethyl-2-vinylazlactone and polyethylene glycol methyl ether methacrylate monomers; n represents the number of repeat units in the polyethylene glycol chain; and the glycidyl groups, the azlactone groups and the polyethylene glycol groups are distributed randomly along the copolymer backbone chain. In some embodiments, the random copolymer comprises no greater than about 30 mole percent of additional monomer.

Random copolymers of this type can be formed into coatings on a substrate to provide a coated substrate comprising: a substrate having a surface; and a film of crosslinked random copolymers on the surface of the substrate, the crosslinked random copolymers having backbone chains comprising polymerized 4,4-dimethyl-2-vinylazlactone monomers, polyethylene glycol methyl ether methacrylate monomer and monomers that provide covalent crosslinks between the backbone chains, the crosslinked random copolymers comprising the structure:

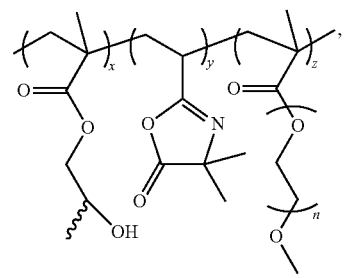

wherein x, y and z represent the mole fractions of the crosslinked monomer, the 4,4-dimethyl-2-vinylazlactone monomer and the polyethylene glycol methyl ether methacrylate monomer; n represents the number of repeat units in the polyethylene glycol chain; / represents a crosslink to another copolymer backbone chain; and the crosslinks, the azlactone groups and the polyethylene glycol groups are distributed randomly along the copolymer backbone.

Coated substrates of this type can provide a cell culture substrate comprising: a substrate having a surface; and a film comprising crosslinked random copolymers on the surface of the substrate, the crosslinked random copolymers having backbone chains comprising polymerized polyethylene glycol methyl ether methacrylate monomers, monomers comprising covalently linked peptide chains, and monomers that provide covalent crosslinks between the backbone chains, the crosslinked random copolymers comprising the structure:

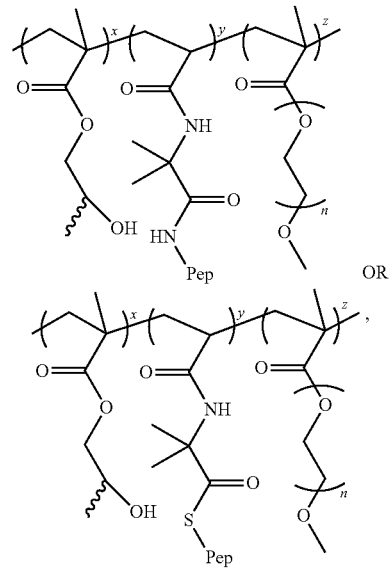

wherein x, y and z represent the mole fractions of the crosslinked monomer, the monomers comprising covalently linked peptide chains and polyethylene glycol methyl ether methacrylate monomers; n represents the number of repeat units in the polyethylene glycol chain; / represents a crosslink to another copolymer backbone chain; Pep represents a peptide chain; and the crosslinks, the peptide chains and the polyethylene glycol groups are distributed randomly along the copolymer backbone.

An embodiment of cell culture substrate can be made by: copolymerizing about 15 to about 35 mole percent 4,4- dimethyl-2-vinylazlactone monomer, about 50 to about 85 mole percent cytophobic polyethylene glycol-containing monomer, and about 1 to about 15 mole percent glycidyl methacrylate monomer to form random copolymers of the three monomers; forming a film of the random copolymers on a surface of a substrate; crosslinking the glycidyl groups on the random copolymers to form a crosslinked random copolymer film; and reacting at least a portion of the azlactone functionalities on the random copolymers with molecules comprising a peptide chain to covalently bind the peptide chains to the random copolymers.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 4. Table. 1: Compositions of random terpolymers of polyethylene glycol methyl ether methacrylate monomers, glycidyl methacrylate monomers and 4,4-dimethyl-2-vinylazlactone monomers (PEGMEMA-r-VDM-r-GMA) made in accordance with Example 1.

DETAILED DESCRIPTION

Random copolymers, crosslinked thin films of the random copolymers and cell culture substrates comprising the crosslinked thin films are provided. Also provided are methods of making and using the copolymers, thin films and substrates.

The copolymers are polymerized from glycidyl methacrylate monomers and vinyl azlactone monomers. The glycidyl methacrylate is present at low concentration and provides the random copolymers with a crosslinking functionality. The vinyl azlactone monomers provide reactive pendant azlactone rings on the random copolymer backbone. The crosslinked thin films are substrate independent, in that they need not be covalently bound to a substrate to form a stable film on the substrate surface. As a result, the thin films can be applied to a wide variety of organic and inorganic substrates.

The azlactone rings on the random copolymers can be reacted with various molecules, including those comprising polypeptides and/or polyethylene glycols, to render the crosslinked thin films suitable for use as cell culture substrates. These substrates provide a chemically defined surface with long-term stability under cell culture processing conditions.

Figure 1:
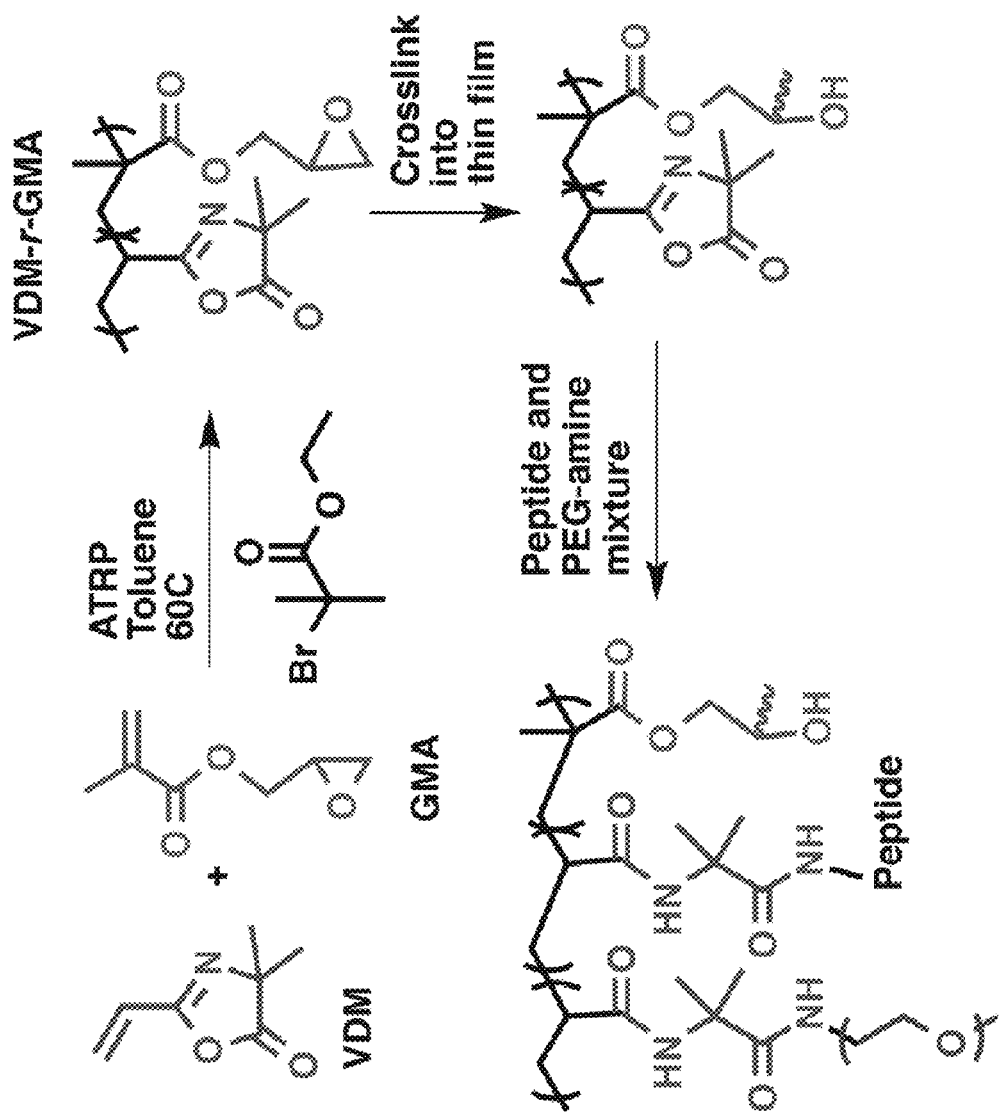
FIG. 1 shows the reaction scheme for the formation of a peptide- and polyethylene glycol-functionalized crosslinked copolymer that is polymerized from glycidyl methacrylate monomers and 4,4-dimethyl-2-vinylazlactone monomers, crosslinked, and then reacted with polyethylene glycol-containing and peptide-containing molecules.

One embodiment of the random copolymers comprises a random copolymer of 4,4-dimethyl-2-vinylazlactone (VDM) and glycidyl methacrylate (GMA) monomers (VDM-r-GMA). The structures of these monomers and a random copolymer polymerized from the monomers is shown in FIG. 1. In that figure, x and z represent the mole fraction of each monomer in the copolymer. Some embodiments of the copolymers consist only of polymerized VDM and GMA monomers. However, other embodiments comprise small amounts of additional monomers. Typically these additional monomers will be present in quantities of no greater than 30 mole %. This includes embodiments in which the additional monomers are present in quantities of no greater than about 20 mol. %, no greater than about 10 mol. %, no greater than about 5 mol. %, no greater than about 1 mol. %, or no greater than about 0.1 mol. %. Hydroxyethyl methacrylate (HEMA), methylmethacrylate (MMA) and poly(vinyl alcohol) (PVA) are examples of additional monomers that can be polymerized into the copolymers. The VDM-r-GMA copolymers may be free of polyethylene glycol monomers polymerized into the copolymer backbone chain. The GMA provides a crosslinking functionality. However, only small quantities of the GMA are needed to provide a stable crosslinked thin film. Therefore, the random copolymers typically comprise from about 1 to about 15 mole % of the GMA monomer and from about 85 to about 99 mole % VMA monomer. This includes random copolymers comprising from about 2 to about 12 mole % of the GMA monomer. The ability to utilize the crosslinking GMA monomer in such low concentrations is advantageous because high concentrations of GMA can lead to non-specific protein and biomolecule adsorption.

Figure 2:
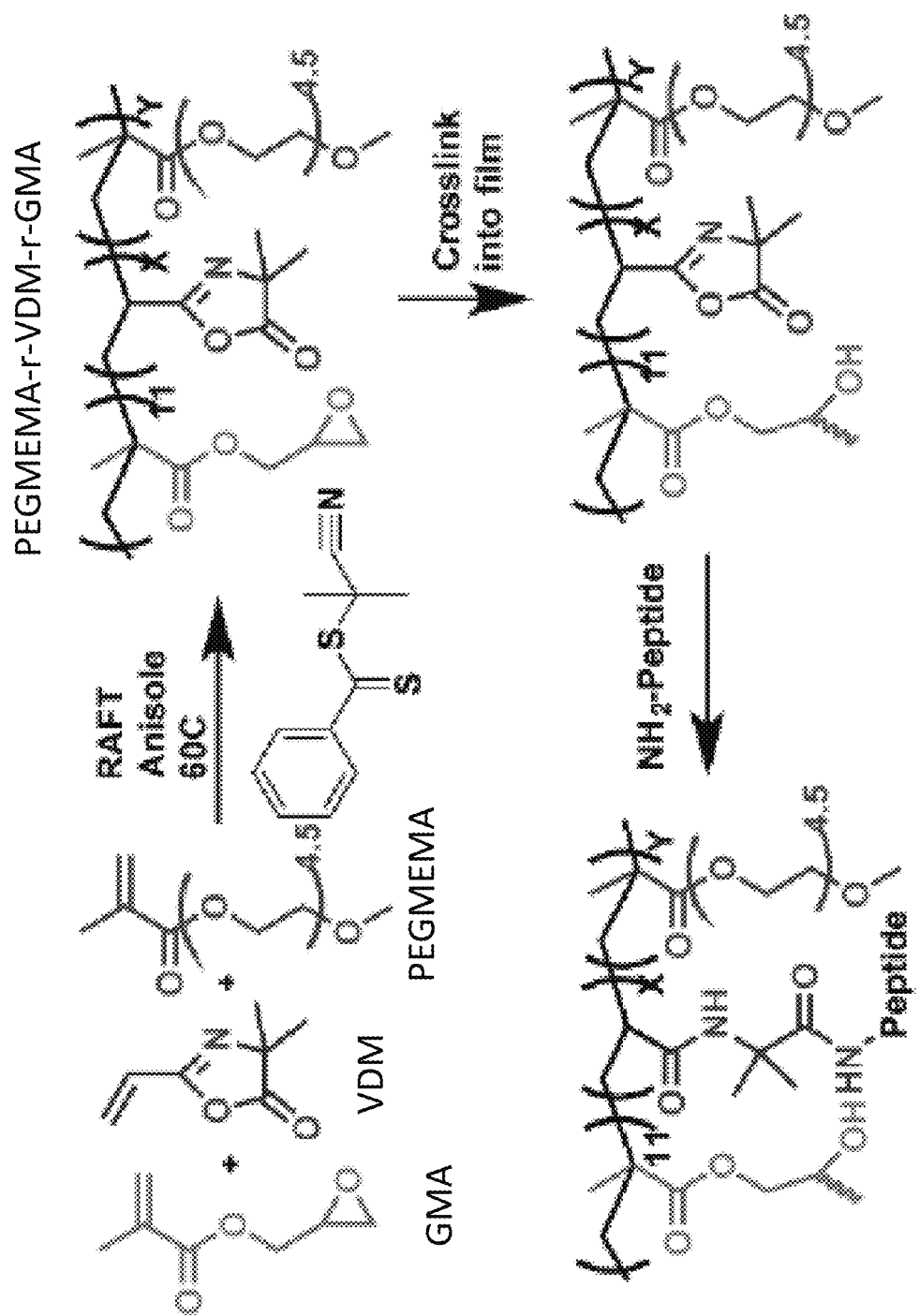
FIG. 2 shows the reaction scheme for the formation of a peptide- and polyethylene glycol-functionalized crosslinked terpolymer that is polymerized from polyethylene glycol methyl ether methacrylate monomers, glycidyl methacrylate monomers and 4,4-dimethyl-2-vinylazlactone monomers, crosslinked, and then reacted with peptide-containing molecules.

Another embodiment of the random copolymers comprises a random copolymer of a cytophobic polyethylene glycol-containing monomer, VDM and GMA monomers. The cytophobic polyethylene glycol-containing monomer confers the copolymers with resistance to the non-specific binding of biomolecules and protein fouling. Polyethylene glycol methyl ether methacrylate (PEGMEMA) is an example of a suitable cytophobic polyethylene glycol-containing monomer. PEGMEMA derivatives, including hydroxyl terminated PEGMEMA, are also examples. The structures of the PEGMEMA, VDM and GMA monomers and a random terpolymer (PEGMEMA-r-VDM-r-GMA) polymerized from the monomers is shown in FIG. 2. In that figure, x and y represent the mole fractions of the VDM and PEGMEMA monomers in the copolymer. In the embodiment shown here, the copolymer comprises about 11 mole percent GMA. Some embodiments of the copolymers consist only of polymerized VDM, GMA and cytophobic polyethylene glycol-containing monomers. However, other embodiments comprise additional monomers. Typically these additional monomers will be present in quantities of no greater than about 30 mol. %. This includes embodiments in which the additional monomers are present in quantities of no greater than about 20 mol. %, no greater than about 10 mol. %, no greater than about 5 mol. %, no greater than about 1 mol. %, or no greater than about 0.1 mol. %. Hydroxyethyl methacrylate (HEMA), methylmethacrylate (MMA) and poly(vinyl alcohol) (PVA) are examples of additional monomers that can be polymerized into the copolymers. As in the VDM-r-GMA copolymers, the GMA in the terpolymers provides a crosslinking functionality and is needed in only small quantities. Therefore, the random copolymers typically comprise from about 1 to about 15% of the GMA monomer. This includes random copolymers comprising from about 2 to about 12% of the GMA monomer. The relative amounts of VDM and cytophobic polyethylene glycol-containing monomers in the copolymers will depend, at least in part, in the desired degree of cytophobicity. By way of illustration only, some embodiments of the random copolymers comprise from about 15 to about 60 mole percent polymerized 4,4-dimethyl-2-vinylazlactone monomer and about 30 to about 85 mole percent polymerized cytophobic polyethylene glycol-containing monomer.

The random copolymers may be copolymerized in solution using a variety of techniques, including free radical polymerization, atom transfer radical polymerization (ATRP), and reversible addition fragmentation chain transfer polymerization (RAFT).

Thin, lightly-crosslinked polymeric films, which can be referred to as mats, are formed by crosslinking the backbone chains of the random copolymers via the pendant epoxy functionalities provided by the GMA monomers. As shown in FIG. 2, the resulting crosslinks comprise the structure —C(O)O—CH$_2$—CH(OH)—. In some embodiments of the crosslinked films all, or substantially all, of the GMA monomers are crosslinked. However it is also possible to retain some residual, unreacted epoxy functionalities. The crosslinked thin films can be formed on a substrate by applying a solution of the random copolymers onto the surface of the substrate and thermally inducing crosslinking reactions to form an insoluble film that can swell in aqueous media. Many suitable techniques for applying a thin layer of the copolymers to a surface are known. These include spin coating and casting techniques, such as doctor blading. Using these techniques, the crosslinked random copolymer films can be formed over very large surface areas. In addition, because the thin films are substrate independent, they can be formed as stable films on many different substrates, including both organic and inorganic substrates. For example, the thin films can be formed on polymeric substrates, such as polycarbonate, polystyrene or polyethyleneterephthalate substrates. They can also be formed on metal, semiconductor and oxide substrates. Specific examples of these include glass, gold and silicon substrates. The substrates may take different forms. For example, the substrate may be a planar or substantially planar substrate, such as might be found in a planar cell culture well. Alternatively, the substrate may be a microcarrier substrate comprising, for example, a plurality of microcarrier beads for use in a suspension culture.

The thinness of the crosslinked random copolymer films helps to render them stable against delamination from the substrate in solution. Thus, the films desirably have a thickness of no greater than about 100 nm (e.g., from about 5 nm to about 100 nm). This includes films having a thickness of no greater than about 50 nm, further includes films having a thickness of no greater than about 30 nm, and still further includes films having a thickness of no greater than about 10 nm. The stability of the thin films can be measured by their ability to resist delamination and degradation in an aqueous solution for an extended period of time. For example, some embodiments of the crosslinked random copolymer thin films do not delaminate or degrade in deionized water at 37° C. for a period of at least 30 days.

Cell culture substrates are formed by covalently bonding peptide chains along the copolymer backbone using polymer-peptide linkers. These linkers can be formed by reacting at least a portion of the pendant azlactone functionalities with peptide-containing molecules via a nucleophilic ring opening of the azlactone. These peptide coupling reactions can take place at room temperature in aqueous media at low peptide concentrations and without activation steps. As illustrated in FIG. 2, the resulting amide linkers comprise the structure —C(O)—NH—C(CH$_3$)$_2$—C(O)—. Suitable nucleophiles for the ring opening reaction include primary amines and thiols. Therefore, the linkers can be formed, for example, via reactions between the azlactone group and the N-terminus of a peptide chain, a lysine side chain or a cysteine side chain.

Figure 3A:
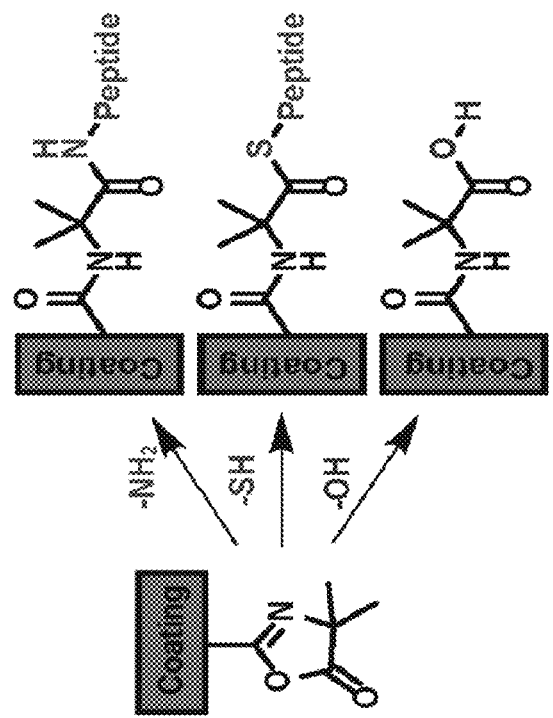
FIG. 3A shows the formation of copolymer linkages formed by reacting an azlactone-functionalized copolymer with an amine-functionalized peptide (upper scheme), a thiol-functionalized peptide (middle scheme), and a hydroxyl group (lower scheme).
Figure 3B:
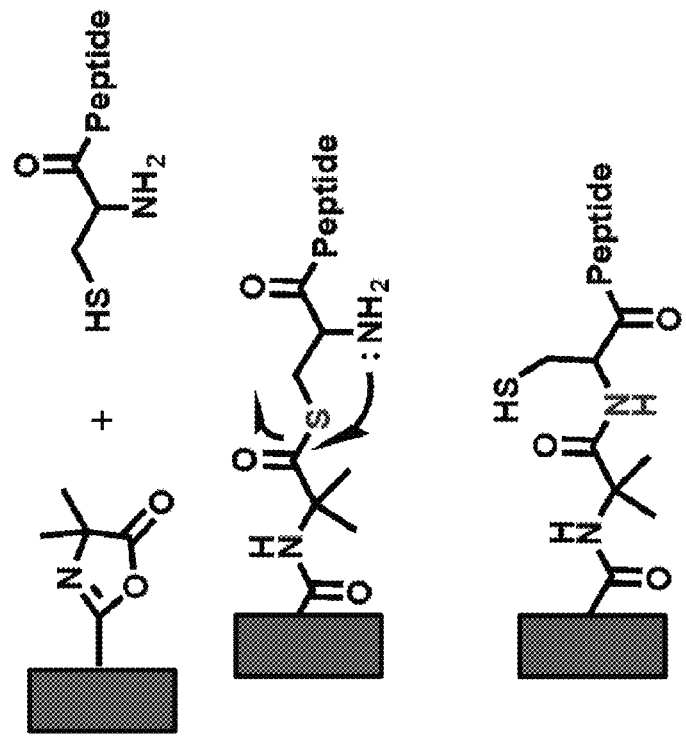
FIG. 3B shows the reaction of the N-terminus of a peptide chain with an azlactone group, followed by rearrangement to form an amide linkage.

A schematic diagram showing polymer-peptide linkers is provided in FIG. 3. The top panel of FIG. 3A shows a polymer-peptide linker formed by reacting a pendant azlactone functionality with an amine-functionalized peptide, while the middle panel shows a polymer-peptide linker formed by reacting a pendant azlactone functionality with a thiol-functionalized peptide to form a thiol ester bond. An N-terminal cysteine on the peptide chain may be particularly useful with the PEGMEMA-r-VDM-r-GMA copolymers. In these systems, the thiol of the cysteine initially reacts with the azlactone group to form a thioester bond. However, due to the proximity of the N-terminal amine, there is molecular rearrangement, to the more favorable and stable amide bond. (Conditions for promoting rearrangement include a 15 minute soak at room temperature in PBS pH 7-8, after initial coupling.) The reaction of the N-terminus of a peptide chain with an azlactone group, followed by rearrangement to form an amide linkage is shown in FIG. 3B.

The polymer-peptide linkages in the cell culture substrates are stable for extended periods under cell culture processing conditions. For example, the polymer-peptide linkers may be stable against peptide detachment for a period of at least 2 days in either of, or both of, phosphate buffered saline (PBS) and minimum essential medium, alpha ($\alpha$MEM)+10% fetal bovine serum (FBS) at 37° C. This includes embodiments in which the polymer-peptide linkers are stable against peptide detachment for a period of at least one week in either of, or both of, PBS and $\alpha$MEM+10% FBS at 37° C., and further includes embodiments in which the polymer-peptide linkers are stable against peptide detachment for a period of at least two weeks in either of, or both of, PBS and $\alpha$MEM+10% FBS at 37° C.

A variety of peptides including very large peptides (i.e., proteins) can be linked to the copolymers, provided they contain a free thiol or amine. For adhesion peptides it may be desirable for the peptides to be: Arg-Gly-Asp-containing peptides (RGD peptides) (cyclic and linear), optionally, with the PHSRN synergy site; Arg-Glu-Asp-Val-containing peptides (REDV peptides); Ile-Lys-Val-Ala-Val-containing (IKVAV peptides), and/or Tyr-Ile-Gly-Ser-Arg-containing peptides (YIGSR peptides). However, other types of peptides can be used, depending on the application. By way of illustration, for growth factor (GF) sequestering KRTGQYKL peptides may be used; for heparin binding TYRSRKY and TYRKKGLQ peptides may be used; for BMP-2 receptor binding EPPSIATSYKLALKTSIVSL peptides may be used; and for VEGF binding KLTWQELYQLKYKGI peptides may be used.

The ability of the cell culture substrates to avoid non-specific binding of biomolecules and protein fouling, even in serum-containing conditions, can be enhanced by covalently binding cytophobic polyethylene glycol (PEG) chains to the copolymer backbone using polymer-PEG linkers. These linkers can be formed by reacting at least a portion of the pendant azlactone functionalities with PEG-containing molecules via pegylation—a base catalyzed ring opening hydrolysis reaction. This may be particularly useful for cell culture substrates comprising the VDM-r-GMA copolymers that lack cytophobic polyethylene glycol-containing monomers. A VDM-r-GMA copolymer having pendant PEG and peptide chains covalently linked along its backbone is shown in FIG. 1. The mole ratio of covalently linked peptide chains to covalently linked PEG chain will depend on the desired degree and location of cell adhesion on the cell culture substrates. By way of illustration only, in some cell culture substrates the mole ratio of the number of covalently linked peptides to the number of covalently linked PEGs will be in the range from about 1:3 to about 0.1:99.9.

The bound peptide chains and/or polyethylene glycol chains may be uniformly distributed on the cell culture substrates, or may be distributed in a regular or irregular pattern, such that one or more regions of the substrate are resistant to cell adhesion by virtue of the presence of cytophobic polyethylene glycol chains, while one or more other regions (e.g., one or more spots) promote biospecific interactions with biological cells by virtue of the presence of the covalently tethered peptides.

The cell culture substrates can be used to culture biological cells by seeding the biological cells onto the cell culture substrate and culturing the seeded cells in an appropriate culture medium under appropriate culturing conditions. Animal stems cells, including mammalian stem cells, are examples of cells that can be cultured using the present substrates. Human stem cells that may be cultured on the cell culture substrate include human mesenchymal stem cells and human embryonic stem cells. However, the cell culture substrates can be used to culture other types of adhesion-dependent cells including, but not limited to, epithelial cells, endothelial cells, epidermal cells, fibroblasts, muscle cells, chondrocytes, osteocytes osteoblasts and adhesion-dependent cancer cells. The cell culture substrates need not be able to promote the growth of the biological cells indefinitely. For the purposes of this disclosure, a substrate is considered to suitable for use a cell culture substrate if it is able to promote cell growth for a period of at least 20 days, as illustrated in Example 1 below.

EXAMPLES

Example 1

This example illustrates a P(PEGMEMA-r-GMA-r-VDM) polymer coating that incorporates VDM chemistry for use as a template for stem cell growth and expansion.

The formation of both thioester and amide polymer-peptide linkers by ring opening of the azlactone is also illustrated. Cyclo Arg-Gly-Asp-Phe-Lys (cRGDfK) or cyclo Arg-Gly-Asp-Phe-Cys (cRGDfC) were used as adhesion molecules and hMSC and H1 embryonic stem cell attachment was examined. Finally, the applicability of these copolymers to coat large area plastic dishes and to passage hMSCs without the use of proteases is demonstrated. Taken together, the results detailed here, show that the copolymer is useful for large area chemically defined growth and expansion of adult and pluripotent stem cells.

Results and Discussion

Design, Synthesis and Coating Formation Process

As a starting point glycidyl methacrylate (GMA) and vinyl azlactone (VDM) were copolymerized to test the copolymerization conditions by living free radical methods. In fact GMA and VDM could be copolymerized by atom transfer radical polymerization (ATRP), reversible addition fragmentation chain transfer polymerization (RAFT), as well as conventional free radical polymerization using azobisisobutyronitrile (AIBN), a common initiator. While this copolymer can be used to introduce both the peptides and PEG chains by ring opening of the VDM with PEG amine and N terminal of the peptides to impart cell-adhesive and nonspecific protein adhesion respectively, the quantification of the relative amount of introduced peptide and PEG molecules can be challenging. Hence, a third comonomer polyethylene glycol methyl ether methacrylate (PEG-MEMA) was introduced to confer nonspecific protein adhesion and allow more accurate quantification both before and after formation of the coating. The tercopolymer P(PEGMEMA-r-GMA-r-VDM) was synthesized by RAFT (FIG. 2) and characterized in solution by proton NMR. The resulting polymer had a molecular weight of over 20 kDa to ensure sufficient chain entanglement. Multiple copolymer compositions with varying amount of VDM but fixed GMA content, were made by RAFT. The copolymer compositions are provided in Table 1, which is shown in FIG. 4. This example focuses on the copolymer containing 24% azlactone, 11% GMA and the remaining 65% PEGMEMA with a molecular weight of 43,094 Da and dispersity of 1.28. The relatively high molecular weight and low dispersity indicates that the reaction is well controlled by RAFT. The controlled synthesis of this copolymer also allows characterization of the relative amount of VDM and GMA in solution before coating. This advantage distinguished the copolymers from those that are polymerized or formed on the surface such as layer-by-layer films as well as commercially available OptiChem® and Synthemax surfaces.

Optimization of Coating Crosslinking

GMA was used to crosslink the thin films. GMA can be annealed at up to 210° C. and as low as 70° C., but in general longer times are required for full crosslinking at low temperature. However, crosslinking at lower temperatures is desirable in order to broaden the applicability of the films to plastic substrates, such as polycarbonate and polystyrene cell culture plates. Plastic culture plates and flasks are used extensively in general cell culture; therefore the ability to simply coat already existing products is advantageous and cost effective. Coatings were fabricated by spin coating the copolymer from an ethanol solution, a solvent tolerant of plastic substrates. For optimization of the crosslinking conditions, silicon was used as the substrate. Crosslinking was carried out at temperatures of 160° C., 110° C. and 85° C. The film was considered fully crosslinked when the film thickness did not change after soaking for an hour in tetrahydrofuran (THF), which is an excellent solvent for the polymer. Complete crosslinking was achieved within 45 minutes at 160° C. The crosslinking was slower at lower temperatures, taking up to 3 hours at 110° C. and up to 24 hours at 85° C.

Physical Stability of the Coating

During the process of cell growth and expansion, the coatings will be immersed in aqueous solution for extended timeframes, and therefore the coating itself should be physically stable. For this system the amount of GMA in the copolymer was 11% to minimize and prevent uncrosslinked chains (physically entangled) from eluting out over time, causing a slow decrease in overall thickness. Here the GMA did provide the coatings with stability, as 92% of the film thickness was retained over a 35 day period while immersed in deionized water at 37° C.

Demonstration of Applicability to a Broad Range of Substrates

Coatings were cast onto gold (Au), silicon, glass, polycarbonate and polystyrene substrates and thermally crosslinked. The static water contact angle of the film remained essentially the same (59 degrees) even though the bare substrates have a range of initial hydrophobic and hydrophilic contact angles. This simple test proved the coating can be formed on many types of substrates.

Azlactone Ring Opening Characterized by PMIRRAS

The chemistry for attachment of the peptides to the azlactone functionality of the stable crosslinked coatings was optimized. In optimizing the chemistry, the goal was to meet the following requirements: achieve peptide coupling in aqueous solution for applicability on polymeric substrates, as organic solvents can severely degraded the substrate; achieve coupling at low concentrations to reduce the peptide cost for large area samples; and achieve quick coupling (within 1-2 hours), as it is desirable to pattern and analyze multiple peptides on a given coating. Typically patterning methods are used as a combinatorial screening tool for multiple compositions, and the lower the time required for functionalization, the lower chance of leakage and cross talk. The reactivity of the azlactone ring was investigated in the coatings using infrared spectroscopy, specifically polarization modulation-infrared spectroscopy (PMIRRAS), to quantify the reactivity of azlactone ring with a nucleophile (—OH, —SH or —NH$_2$, FIG. 3).

Figure 5:
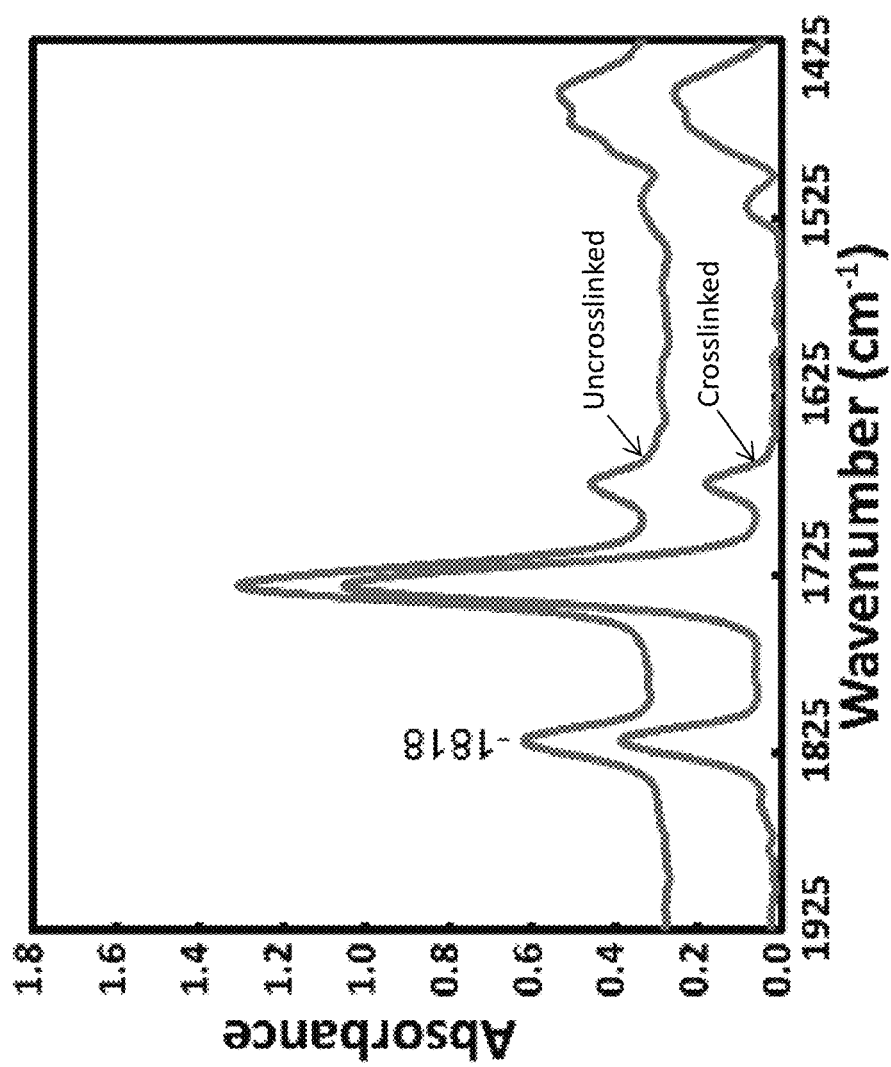
FIG. 5 shows the PMIRRAS analysis of PEGMEMA-r-VDM-r-GMA on a gold substrate before and after crosslinking via the polymerized GMA monomers.

To evaluate the effect of high temperature (110° C.) crosslinking, if any, on the azlactone functionality, the crosslinked and uncrosslinked films were compared by PMIRRAS. FIG. 5 shows that the carbonyl peak at 1818 cm$^{-1}$ from the azlactone ring was still intact after the crosslinking. The peak located at 1818 cm$^{-1}$ completely disappeared after only one hour reaction at room temperature (FIG. 6), and new peaks at 1661 cm$^{-1}$ and 1525 cm$^{-1}$ from amide linkages emerged.

Figure 6:
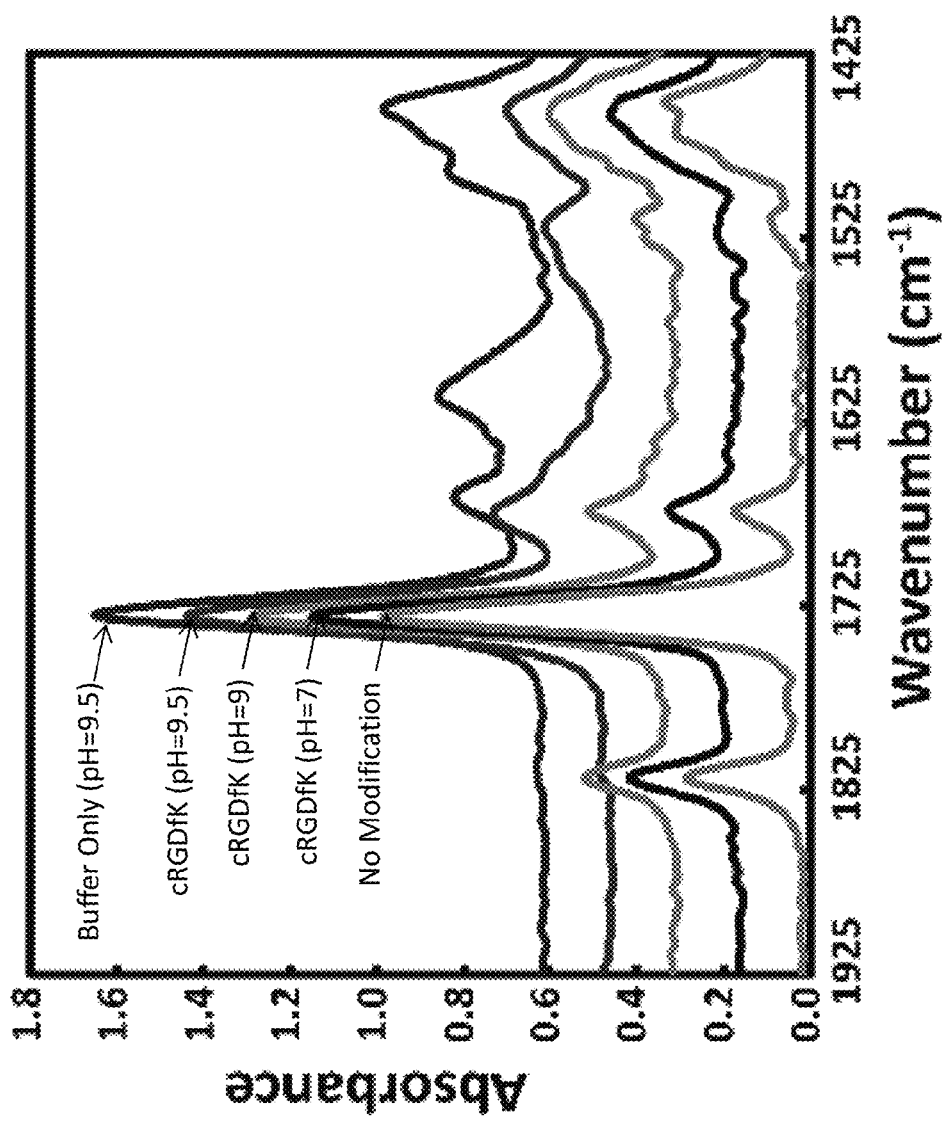
FIG. 6 shows the PMIRRAS analysis of PEGMEMA-r-VDM-r-GMA on a gold substrate after reacting with cRGDfK peptide at various pHs.

Next, the reactivity of the cell adhesive peptide cRGDfK through the lysine side chain was examined. As a logical starting point coupling in phosphate buffered saline (PBS) at pH 7.4 was attempted, as this is a very common buffer used in cell culture. At neutral pH (7.4) and concentrations of 10 mM or lower, the azlactone ring did not open at room temperature, even when reacted for 24 hours. It is likely that at low concentrations of peptide the reaction kinetics is slow and the PEG side chains may pose steric barrier for the deprotonated amine to react with the azlactone ring. To facilitate amine coupling at 10 mM concentration, 1.5 M sodium sulfate was added, and the pH was raised to increase the amount of bound peptide (FIG. 6). The cRGDfK peptide did not react significantly within 1 hour, until the pH was raised to 9.5, then the peak at 1818 cm$^{-1}$ completely disappeared (FIG. 6). Coupling was confirmed by the emergence of amide peaks at 1661 cm$^{-1}$ and 1535 cm$^{-1}$. As a control the coating was incubated in pH 9.5 buffer for 1 hour, in the absence of the amine, and complete hydrolysis of the azlactone ring was observed, leading to the emergence of a carboxylate peak at 1610 cm$^{-1}$. This suggests at basic pH there is a competition between amines and hydroxyl groups to open the azlactone ring.

Figure 7:
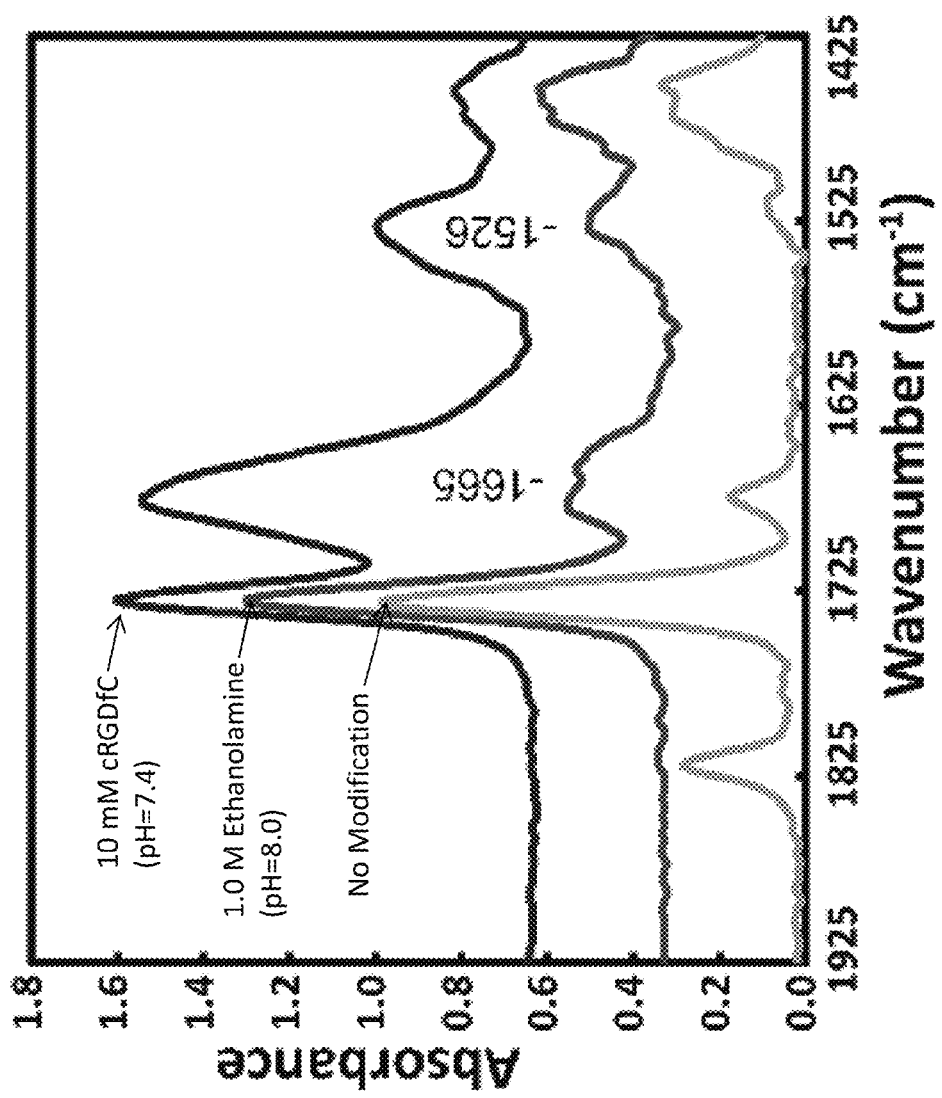
FIG. 7 shows the PMIRRAS analysis of PEGMEMA-r-VDM-r-GMA on a gold substrate before and after reacting with 1.0 M ethanolamine and cRGDfC peptide.

A comparable peptide cyclic cRGDfC was reacted for 1 hour at 1 mM in PBS at pH 7.4 (FIG. 7). Surprisingly the peak at 1818 cm$^{-1}$ completely disappeared and two very strong amide peaks appeared. The polymer peptide linker here was a thioester bond, the two amide bonds appeared due to the peptide backbone. The intensity of the amide peaks showed that thiols react faster and more completely with azlactones than amines at neutral pH and at low concentrations.

XPS Analysis of Thin and Thick Coatings

To further probe the reaction of the copolymer coating with cRGDfC and cRGDfK, X-ray photoelectron spectroscopy (XPS) was performed. XPS is a common surface characterization tool that can be used to determine the surface coverage of small molecules. In a blank coating, elements carbon (C), oxygen (O), and nitrogen (N) were present. Each azlactone ring has 1 nitrogen atom (N), which provides a marker to calculate the theoretical maximum peptide concentration. The concentration used for solution coupling was decreased from 8.4 mM, 0.84 mM, and 0.084 mM and the percent coupled compared for cRGDfK and cRGDfC peptides. The reaction time was kept to 1 hour at room temperature. The results show that peptide concentrations as low as 0.084 mM for cRGDfK, and 0.84 mM for cRGDfC, can be used without adversely affecting the reaction efficiency. In agreement with the PMIRRAS data, the XPS analysis also supports more efficient reaction of thiols over amines with azlactone.

Figure 8:
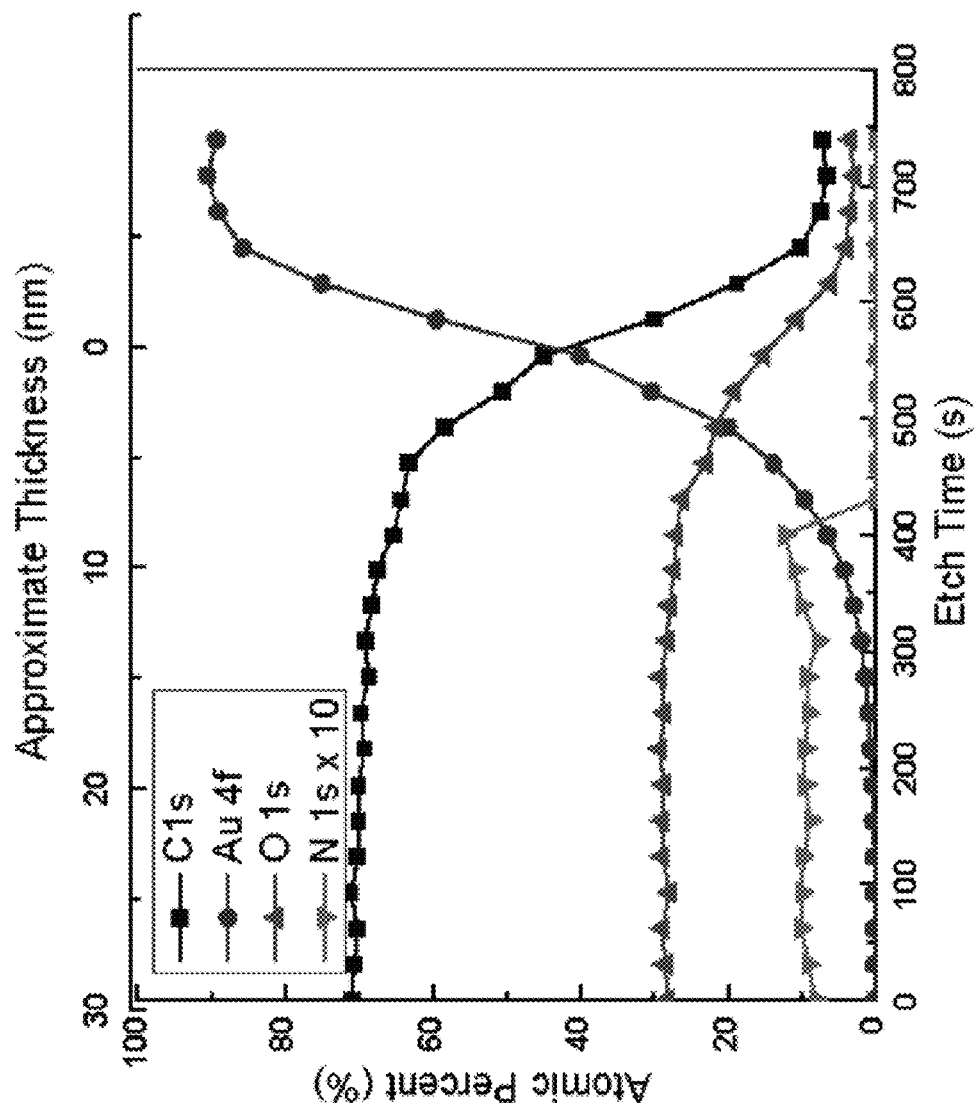
FIG. 8 shows the results of XPS depth profiling on a crosslinked film of PEGMEMA-r-VDM-r-GMA prior to coupling with cRGDfK peptide.
Figure 9:
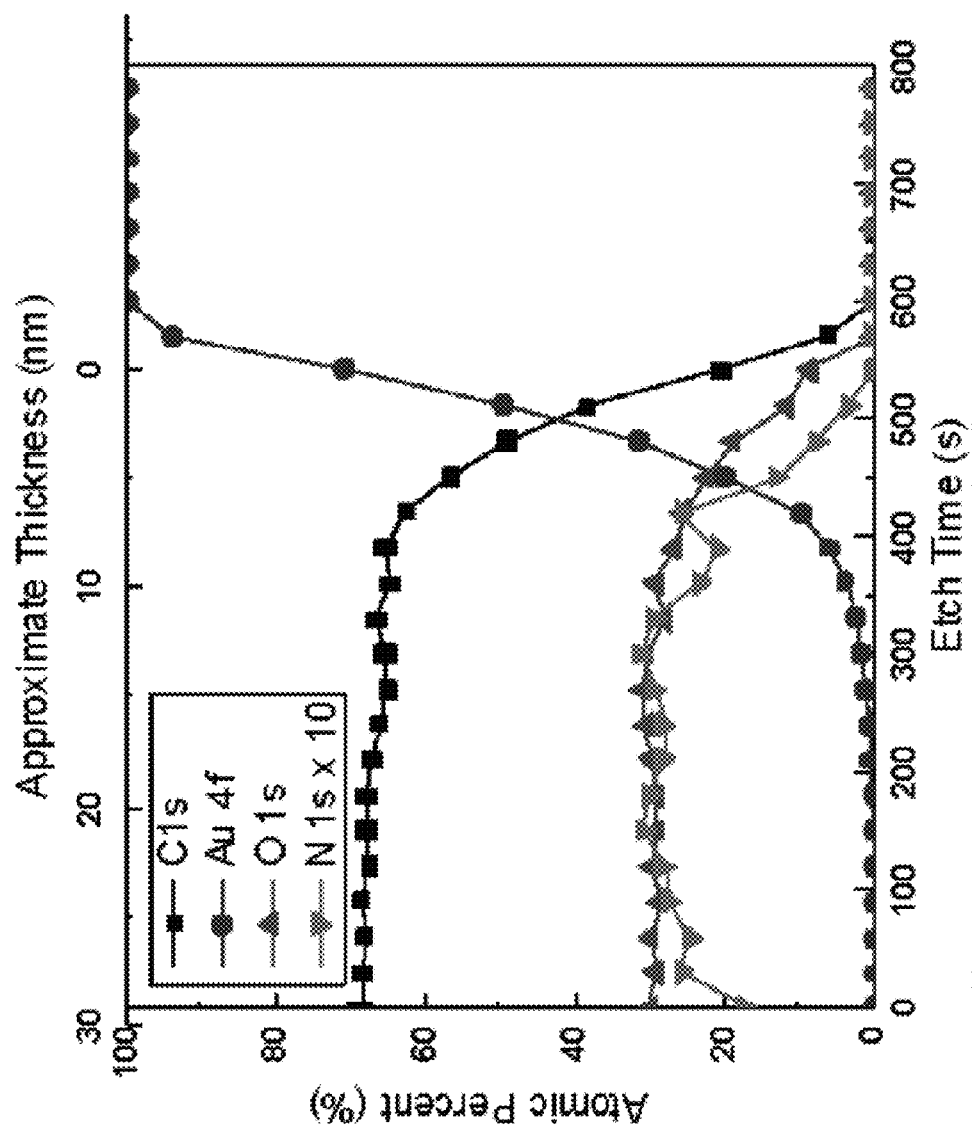
FIG. 9 shows the results of XPS depth profiling on a crosslinked film of PEGMEMA-r-VDM-r-GMA after coupling with cRGDfK peptide.

XPS typically samples 10 nm into the thickness of the film. Since the crosslinked coatings are post-functionalized with peptides it is important to understand the spatial distribution of the peptides. To study this depth profiling using large Argon clusters with a etch rate of 0.05 nm/sec was used, and XPS data was acquired every 1.5 nm. In XPS depth profiling, the top layer of the material is continuously removed while XPS spectra is being acquired. The azlactone content in an unmodified film was quite uniform throughout the thickness of the layer FIG. 8. The increase in the amount of nitrogen after coupling (FIG. 9) was due to the amide bonds in the peptides. In fact, throughout the 30 nm thickness the peptide was relatively well distributed, indicating that the peptides diffuse and bind throughout the depth of the coating.

Figure 10:
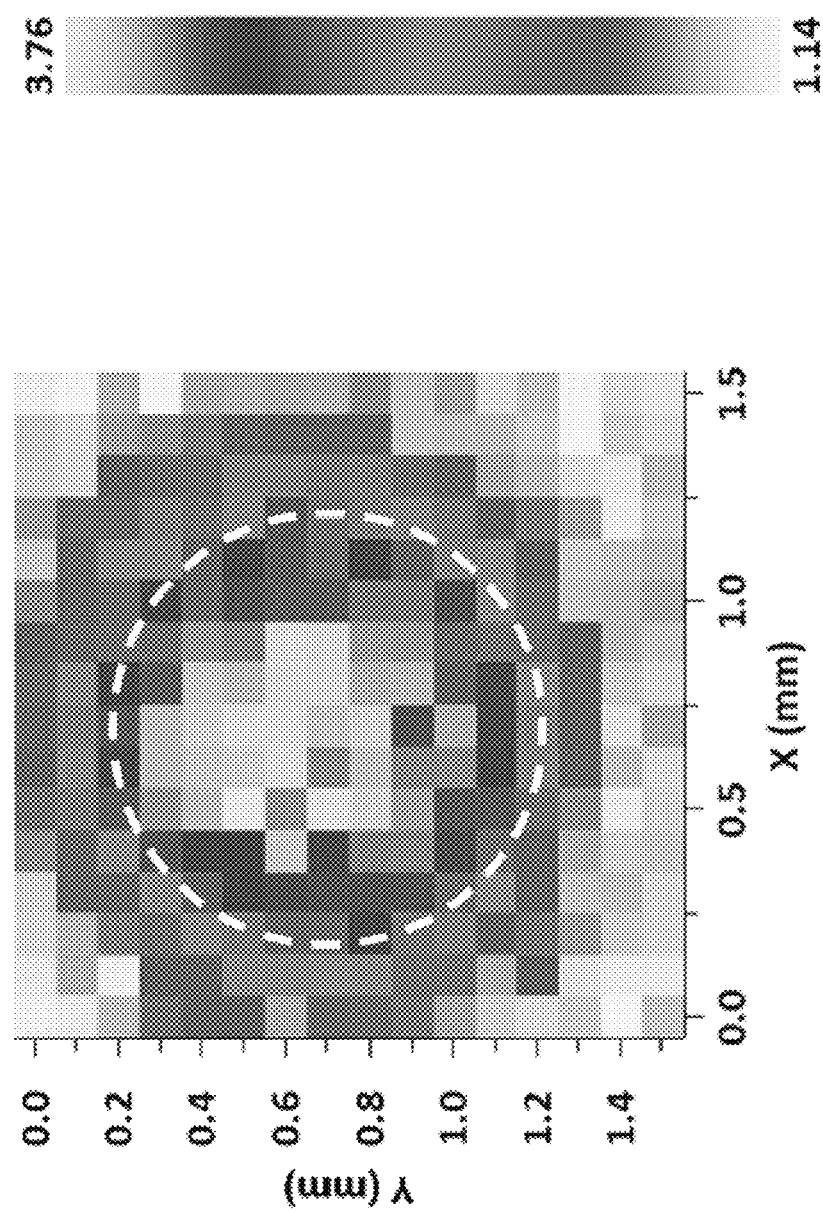
FIG. 10 is an XPS map showing the atomic percent of nitrogen over a 1.5 mm$^2$ area of a crosslinked film of PEGMEMA-r-VDM-r-GMA after coupling with cRGDfK peptide.

To visualize the localization of the cRGDfK peptide, the atomic percent of nitrogen on the surface of the coating was mapped (FIG. 10) using the XPS mapping function. An elastomeric template (PDMS) was used to create a 1.1 mm diameter spot of the peptide. Element mapping of N (1s) atomic percent over the 1.5 mm$^2$ area shows the center of the spot at 3.76 atomic % and the background area at 1.14%. The atomic percents obtained are in good agreement with the depth profiling studies and clearly indicate the peptide can bind the coating in a PDMS stencil.

Coatings for Controlled Stem Cell Attachment

After characterization of the coating and optimization of the azlactone peptide coupling, cell adhesion experiments were preformed to test the effectiveness of the template as a cell culture substrate. The hMSC adhesion to both cRGDfK and cRGDfC, passage of hMSCs on the coating, and the stability of thioester versus amide bonds in aqueous environments were investigated.

Stem Cell Attachment to Cyclic Peptides

Figure 11:
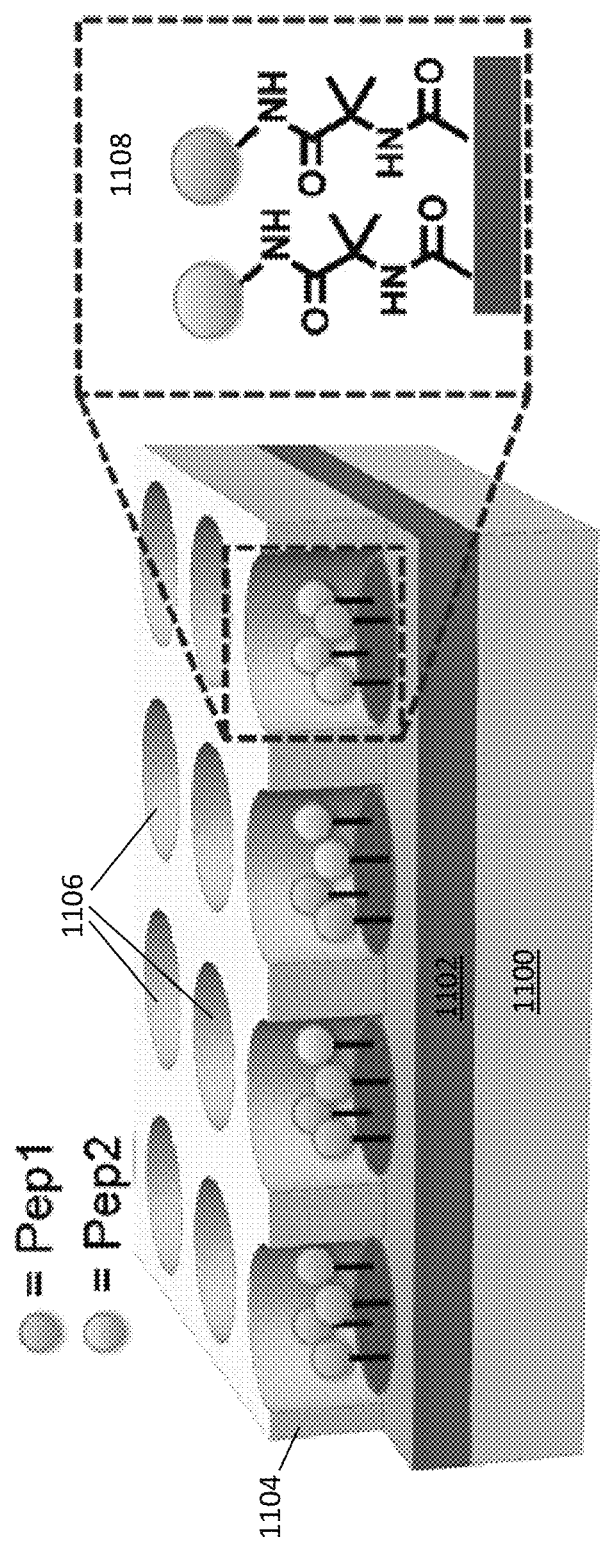
FIG. 11 is a schematic diagram of a crosslinked PEG-MEMA-r-VDM-r-GMA that has been patterned with spots of bound peptide using an elastomeric template as a mask.
Figure 12:
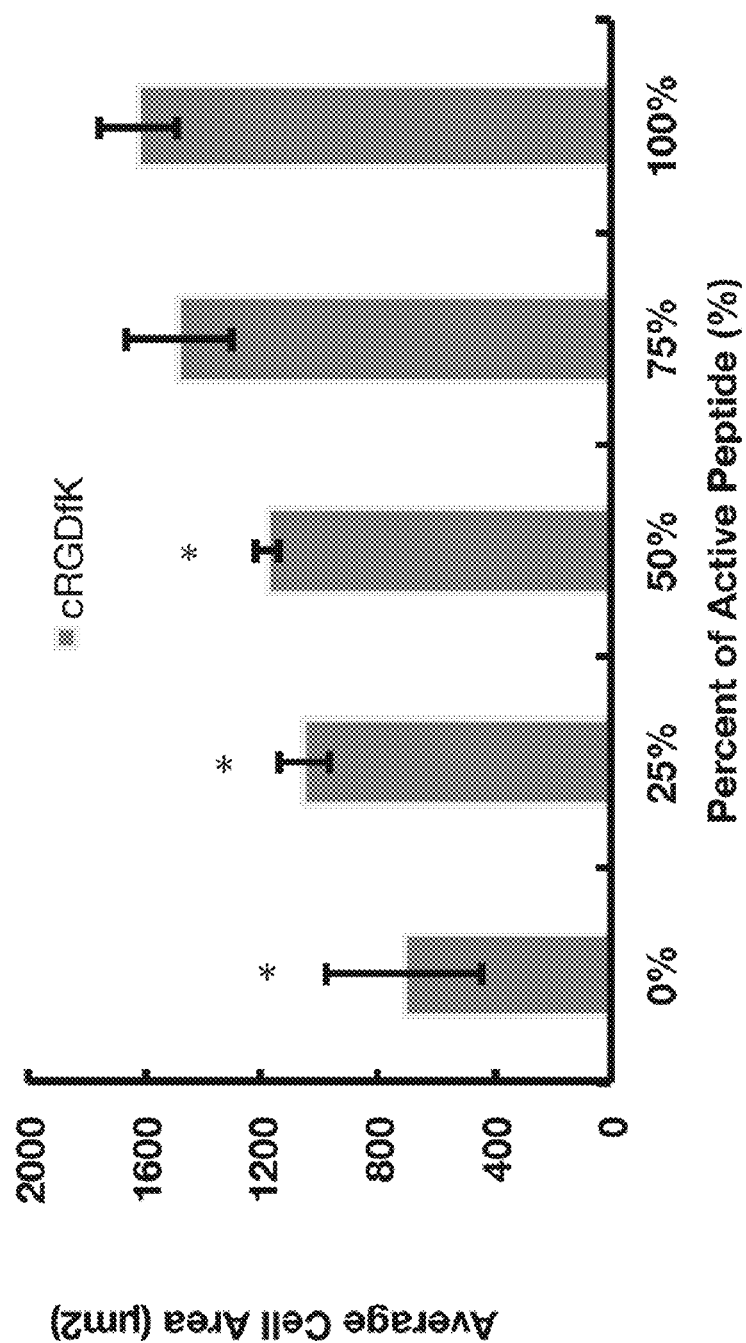
FIG. 12 shows the average projected cell area of hMSCs on a cell culture substrate comprising covalently linked cRGDfK peptide.
Figure 13:
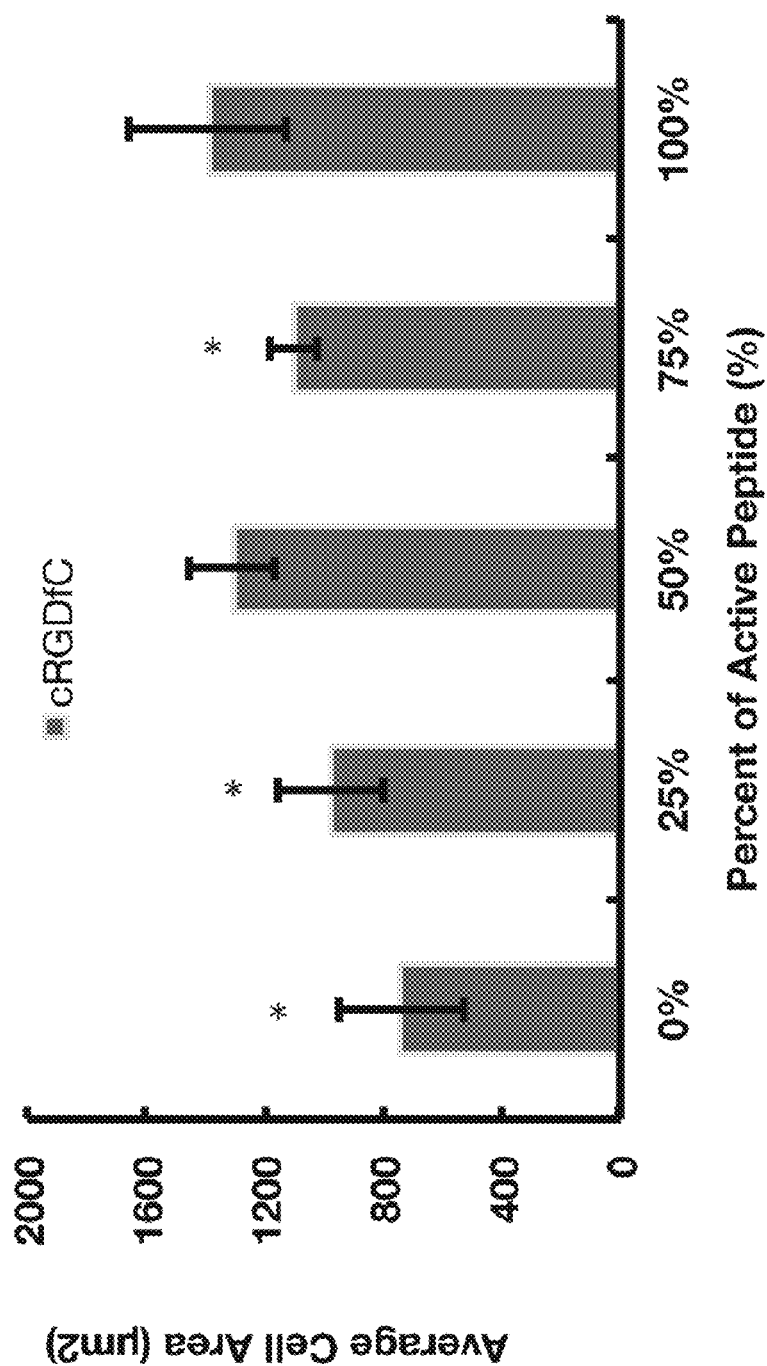
FIG. 13 shows the average projected cell area of hMSCs on a cell culture substrate comprising covalently linked cRGDfC peptide.

An elastomeric template was used to pattern multiple peptide combinations at once into small 1.1 mm diameter spots on the crosslinked film (coating). The patterned structure, shown schematically in FIG. 11, included the plastic (polycarbonate) substrate 1100, the crosslinked random copolymer film 1102, the elastomeric template 1104 defining a plurality of spots 1106, and peptide chains 1108 covalently linked to crosslinked random copolymer 1102 film in spots 1106. In the 1.1 mm diameter spots, 1.3 µL, of a solution of a mixture of adhesive and non-adhesive scramble peptide (overall peptide concentration constant at 1 mM), was pipetted. This effectively lowered the total amount of adhesive peptide on the surface while keeping the total peptide content the same. Seeding and culture of hMSCs in the presence of 10% fetal bovine serum (FBS) showed an insignificant amount of non-specific cell adhesion to the non-adhesive cRADfK or cRADfC spots (0% condition) and to the surrounding coating (unmodified). The results showed attachment and spreading of hMSCs on the spots after 6 hours with increasing amount of adhesive peptide. To quantify cell attachment, hMSCs were allowed to attach for 20 hours on large area samples (1 inch by 0.5 inch) before they were fixed and stained for the actin cytoskeleton. For both the peptides cRGDfK and cRGDfC (FIGS. 12 and 13, respectively), the hMSC projected cell area directly correlated with the amount of peptide present on the coating, as RGD density increased, the cells increased in projected area. In general, cells with areas of 800 cm$^{-1}$ and lower were not well spread and most likely did not have extended lamellipodia.

Chemically Defined Passage of hMSCs

The ability to passage hMSCs off the coating and reseed them back down onto the same coating could have a large impact on bio manufacturing and the therapeutic applications of hMSCs. Using Versene solution (Life Technologies) on cRGDfK functionalized coatings on large area polystyrene dishes (150 cm$^2$) the effectiveness of passaging hMSCs was examined. hMSCs were grown on the coating coupled with cRGDfK for 3 days in αMEM with 10% FBS. Versene solution was then used to successfully passage off the surface and back onto the same substrate. Successful reseeding onto the same substrate containing both adhesive (cRGDfK) and non-adhesive (blank coating) areas, shows that the substrate was unaltered by the Versene treatment. Further, cell culture with 10% FBS (which contains many proteins and growth factors) provides a good test for surface fouling during the process.

Versene solution is a phosphate buffered saline (PBS) solution containing 0.48 mM ethenediaminetetraactetic acid (EDTA). EDTA is a chemically defined agent used usually in combination with trypsin for hMSC passage. Upon application, EDTA binds the Calcium and Magnesium ions and therefore interferes with the integrin structure, physically disrupting the ability of the cell to bind to the peptides on the surface. However, EDTA has not been shown to be effective for passaging hMSCs on TCPS alone without a protease such as trypsin. Supposedly chemically defined interaction of the hMSCs with the coating allows for passaging with Versene. The cRGDfK peptide is known to bind to αvβ3 integrins and potentially αvβ5 and α5β1 integrins as well. (See, Mas-Moruno, C.; Rechenmacher, F.; Kessler, H., Cilengitide: The First Anti-Angiogenic Small Molecule Drug Candidate. Design, Synthesis and Clinical Evaluation. *Anti-Cancer Agents in Medicinal Chemistry* 2010, 10, 753-768 and Shuhendler, A. J.; Prasad, P.; Leung, M.; Rauth, A. M.; DaCosta, R. S.; Wu, X. Y., A Novel Solid Lipid Nanoparticle Formulation for Active Targeting to Tumor αvβ3 Integrin Receptors Reveals Cyclic RGD as A Double-Edged Sword. *Advanced Healthcare Materials* 2012, 1, 600-608.) It was concluded, therefore, that EDTA was able to disrupt these integrins, allowing for cell detachment. The ability to coat large plastic dishes, grow hMSCs, and passage them using a chemically defined agent (Versene), makes it feasible to conduct fully chemically defined culture and passaging of hMSCs.

Evaluation of Coating-Peptide Stability in Culture Conditions

Figure 14:
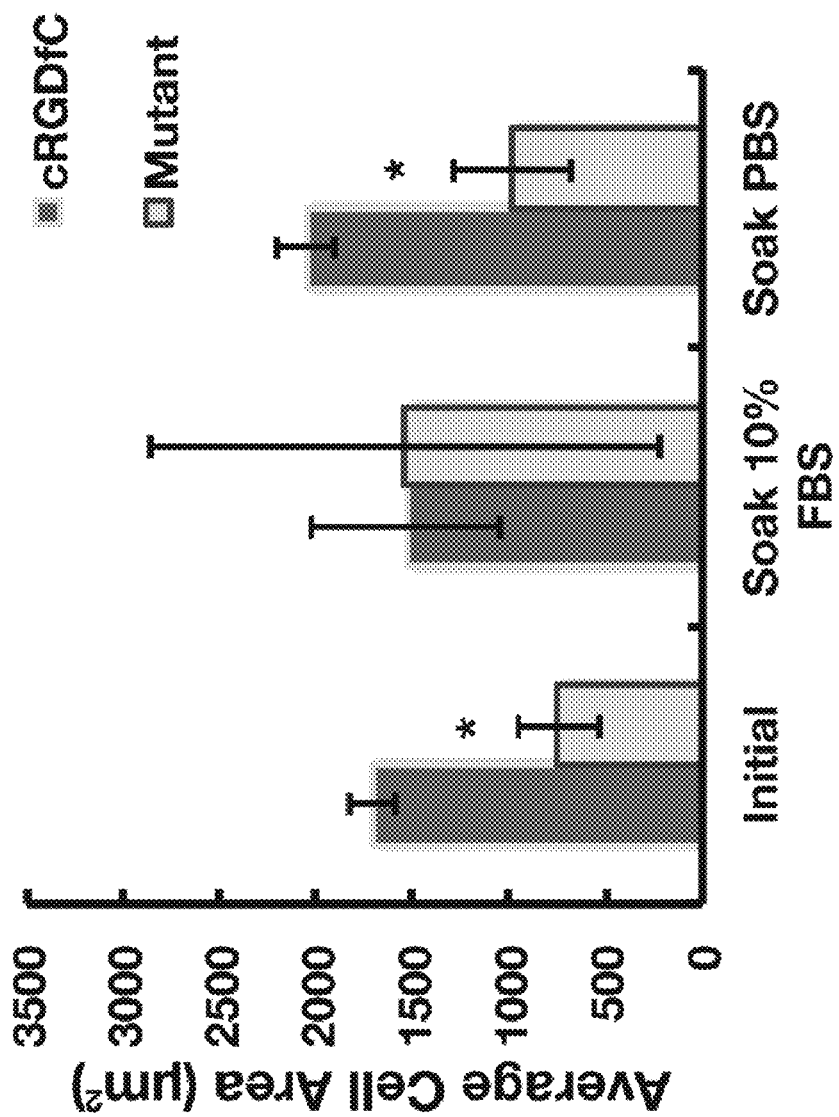
FIG. 14 shows the shows the average projected cell area of hMSCs on a cell culture substrate comprising covalently linked cRGDfC peptide without pre-soaking, after soaking in MEM+10% FBS for two weeks prior to seeding the hMSCs, and after soaking in PBS for 1 week prior to seeding the hMSCs.
Figure 15:
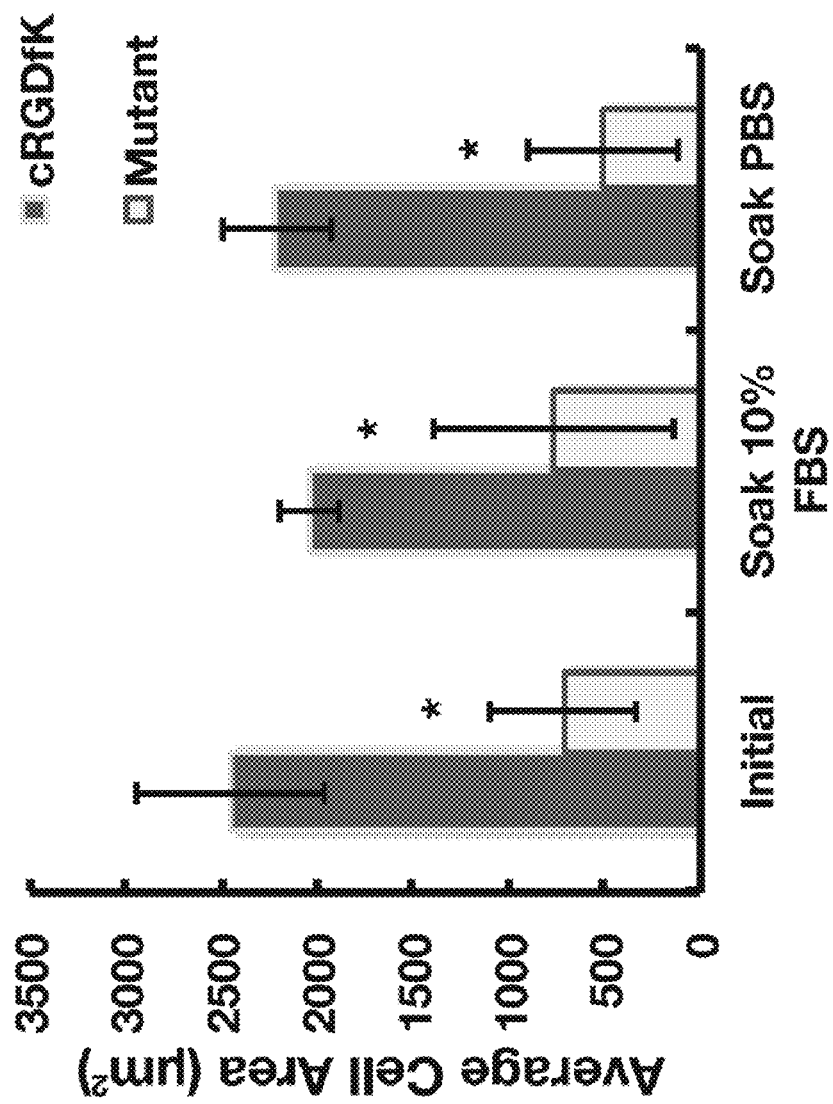
FIG. 15 shows the shows the average projected cell area of hMSCs on a cell culture substrate comprising covalently linked cRGDfK peptide without pre-soaking, after soaking in MEM+10% FBS for two weeks prior to seeding the hMSCs, and after soaking in PBS for 1 week prior to seeding the hMSCs.

An initial goal of the design of VDM containing copolymers was to investigate the stability of the peptide-polymer linker. Hence, the stability of the coating-peptide linker (either amide or thioester) was assessed by soaking experiments in both PBS and αMEM+10% FBS for 2 weeks. The average hMSC area on spots patterned with either the adhesive peptide or the non-adhesive scramble was examined. By first soaking the coating and then seeding hMSCs, followed by XPS analysis, the following conclusions regarding the stability of the peptide/polymer link were reached: 1) the amide linkage was stable under both serum and PBS conditions (FIGS. 14 and 15 for cRGDfC and cRGDfK, respectively); 2) the thioester linkage, though stable in PBS at the same pH, is labile in serum containing conditions; and 3) thiols are more efficient in ring opening the azlactone compared to amines, but the thioester bond is more labile under serum conditions. Mechanism of loss could be due to hydrolysis or more likely proteases present in the serum, and/or displacement by primary amines. In fact the labile nature of the thioester bond can be used advantageously to design dynamically cell responsive surfaces.

Pluripotent Cell Attachment

The utility of this coating is not limited to hMSCs. Pluripotent cell type (H1 embryonic stem cells) were also cultured on the cRGDfK peptide patterned into 1.1 mm diameter spots. H1s were seeded with ROCK inhibitor (a Rho-associated protein kinase) in E8 media at a high density. H1's remained on the surface for 4 days and were confluent on the spots by hour 36. As a control the scramble cRADfK peptide did not show adhesion of H1s, confirming that the cells were interacting specifically with the active cRGDfK peptide. H1 pluripotency after culture was not tested in this study, however these initial results demonstrate the broad applicability of this coating in other areas of stem cell biology.

Conclusions

The PEG based copolymer designed herein, provides a well defined template for stem cell culture and passage. The crosslinking of the coating allows for its use on many different substrate types including plastic (polystyrene, polycarbonate), silicon, glass and gold substrates.

Experimental Design

Materials.

Poly(ethylene glycol) methyl ether methacrylate (PEG-MEMA, Mn~300 g/mol), glycidyl methacrylate (GMA), 2-cyano-2-propyl benzodithioate, 2,2'-azobis(2-methylpropionitrile), anisole, acetone, sulfuric acid ($H_2SO_4$), hydrogen peroxide 30% in water ($H_2O_2$), cyclopentanone, and ethanol (EtOH) were purchased from Sigma Aldrich Co. 2-Vinyl-4,4-dimethyl azlactone (VDM) was a gift from Dr. Steve Heilmann from the 3M Corporation. (Milwaukee, Wis.). Silicon wafers (<100>, p-type) were purchase from University Wafer (Boston, Mass.). Human mesenchymal stem cells (hMSCs) were from Cambrex (North Brunswick, N.J.). Minimum essential medium, alpha (1×; αMEM) was from CellGro (Mannassas, Va.). Trypsin (0.05%) and penicillin/streptomycin were from Hyclone (Logan, Utah). VDM and GMA were purified by vacuum distillation. All other materials were used as received.

Polymer Synthesis.

Copolymers P(PEGMEMA-r-GMA-r-VDM) were synthesized by RAFT polymerization. In a typical synthesis PEGMEMA (8.3 mmol, 2.49 g), GMA (0.7 mmol, 99.5 mg), VDM (1 mmol, 139.2 mg), are added to a 25 mL Schlenk flask. The solvent anisole (13.6 mL) was added at a monomer to solvent ratio of 1:5. The chain transfer agent (CTA), 2-cyano-2-propyl benzodithioate (0.01 mmol, 2.2 mg) was added at a total monomer to chain transfer agent ratio of 1000:1. Last the initiator 2,2'-azobis(2-methylpropionitrile), (0.01 mmol, 1.6 mg) was added at a initiator to CTA ratio of 1:1. The mixture was degassed with three freeze-pump-thaw cycles. Polymerization was allowed to proceed at 60° C. for 18 hours, after which the mixture was precipitated in n-hexanes and redissolved in tetrahydrofuran three times. The resulting light pink copolymer was stored in tetrahydrofuran at −20° C. P(PEGMEMA-r-GMA-r-VDM) was analyzed using gel permeation chromatography (GPC) and proton nuclear magnetic resonance spectroscopy ($^1$H-NMR).

Substrate Preparation.

Glass microscope slides purchased from Fisher Scientific were cut into thirds. Silicon and glass substrates were then sequentially cleaned by sonication in deionized (DI) water, ethanol for 5 minutes each and then dried in a stream of air. Following, substrates were placed in a piranha solution (3:1 $H_2SO_4:H_2O_2$) at 95° C. for 30 minutes, washed with DI water and ethanol, and used within 24 hours of cleaning Caution! Piranha reacts violently in contact with organic matter. Polycarbonate substrates (GraceBio, HybriSlip 22 mm×22 mm), sterile treated tissue culture dishes (Fisher Scientific), and gold substrates (EMF, 50 Å Ti, 1000 Å Au) were rinsed with DI water and ethanol and used directly.

Film Formation and Crosslinking.

Copolymers were diluted in 100% ethanol (Decon Labs) and spin coated onto the prepared substrates. The concentration of the copolymer was 12 mg/mL to achieve thickness of 30 nm. Films were promptly annealed for 45 minutes at 160° C. to crosslink the film or at 110° C. for 3 hours or 85° C. for 24 hours, all under vacuum.

Coating Stability.

Coatings with thicknesses of 30 nm were crosslinked at 160° C. and put into either deionized (DI) water for 38 days while incubated at 37° C. Periodic replacement of the aqueous solution was done every 3-4 days. Dry coating thickness was determined at designated time points by ellipsometry using a Rudolph Auto EL null ellipsometer. Measurements were made at designated time points after drying the films under vacuum overnight using an angle of incidence of 70° and FilmEllipse® software version 1.1 (Scientific Company Intl.).

Contact Angle.

Measurements were made on 30 nm coatings crosslinked onto gold, glass, silicon and polycarbonate substrates using a Dataphysics OCA 15 Plus instrument with an automatic liquid dispenser at ambient temperature. Static water contact angles were measured with a 5 µl droplet of deionized water in 5 different locations on the coatings. The advancing and receding contact angles were measured and the data are reported as the average with standard deviation. The same was done for uncoated, bare substrates for comparison.

Elastomeric Stencil Formation.

Elastomeric stencils were created using a soft lithography process already reported in the literature. Briefly, a master mold was created from SU-8 100 spin coated onto a silicon wafer and the pattern was transferred using conventional photolithography techniques. To prepare the polydimethylsiloxane (PDMS), a 1 to 10 ratio of base to curing agent (w/w) was mixed and degassed for 1 hour. The mixture was cast over the master mold and cured for 6 hours at 85° C. The resulting PDMS template was cleaned by solvent extraction in hexanes overnight.

Peptide Immobilization.

Coatings were washed with PBS at pH 7.4 prior to peptide coupling. The cRGDfC peptides were coupled at either 0.084 mM, 0.84 mM, or 8.4 mM in PBS at pH 7.4 for 1 hour. The cRGDfK peptide was coupled a the same concentrations only in a 0.25M sodium phosphate buffer at pH 9.5 with 1.5 M sodium sulfate. For PMIRRAS this pH was adjusted up from pH 7.4 with HCl. The solution was bubbled on top of the coating at room temperature and covered to prevent evaporation. This was followed by three 10 minute rinses with deionized water. For patterning, elastomeric templates with 1.1 mm diameter spots were placed atop the coating on the desired substrate. The spots were then filled with 1.3 µL, and covered to prevent evaporation for 1 hour. After, the solution was aspirated and replaced with deionized water (1.3 µL) three times. Then the elastomeric template was removed, and the coating soaked in PBS for 1 hour. Samples for cell culture were sterilized with 70% ethanol for 20 minutes, transferred to a new sterile 6-well plate, and rinsed three times with sterile PBS to remove ethanol.

PMIRRAS Analysis.

Gold substrates (1000 Å, EMF Corporation, TA134) coated with the copolymer were placed at incident angle of 83° in a Nicolet Magna-IR 860 Fourier transform IR spectrophotometer equipped with a photoelastic modulator (PEM-90, Hinds Instruments, Hillsboro, Oreg.), a synchronous sampling demodulator (SSD-100, GWC technologies, Madison Wis.) and a liquid nitrogen cooled mercury-cadmium-telluride detector. The modulation was set at 1600 $cm^{-1}$ and 500 scans were obtained for each sample with a resolution of 8 $cm^{-1}$. The differential reflectance IR spectra were then normalized and converted to absorbance spectra using OMNIC software.

XPS Analysis.

The measurements were performed with a Thermo Scientific Model K-Alpha XPS instrument using monochromatic Al Kα radiation (1486.7 eV). The instrument uses a hemispherical electron energy analyzer equipped with a 128 multi-channel detector system. Survey spectra and high-resolution spectra were acquired using analyzer pass energies of 200 eV and 50 eV, respectively. The X-ray spot size was 400 µm for single point analysis. Depth profiling was done using large Argon clusters with 4000 eV for etching and data was collected every 30 seconds using the snap capture function. Data was analyzed using Avantage XPS software package. Peak fitting was performed using Gaussian/Lorentzian peak shapes and a Shirley/Smart type background. At least three points were taken per sample and the averages and standard deviations are reported.

Cell Culture.

The hMSCs (Lonza, Cat PT2501) were expanded at low density on tissue culture treated polystyrene plates. At passage 6 the cells were harvested using a 0.05% trypsin solution and suspended in 1 mL of αMEM. In a rectangular 6-well plate, 4 mL of αMEM containing 1% penicillin/streptomycin and 10% MSC qualified fetal bovine serum (FBS) (HyClone Cat# SH30070) was added. hMSCs were seeded at 5,000 cells per $cm^2$ into each well for patterned peptide spots and 7,000 cells per $cm^2$ for large area coatings. Wells were then gently rocked to evenly distribute the cells. Cells were incubated at 37° C. and 5% $CO_2$ to promote cell attachment for 6 hrs. At the end of the attachment period, the medium was aspirated from the wells and gently washed with sterile 1×PBS (pH 7.4) to remove any dead or loosely attached cells, after which cells were fixed with 3.7% formaldehyde in PBS buffer for 15 minutes.

Immunohistochemistry.

Staining of the actin cytoskeleton and nuclei was performed as directed by the manufacturer (catalogue no. FAK100, Millipore, Mass.). Substrates were then washed with a solution containing 0.05% Tween 20 in a 1×PBS solution. Cells were permeabilized using 0.1% Triton X-100 in 1×PBS for 5 min. The mats were rinsed twice with a wash buffer and then blocked to prevent nonspecific antibody adsorption using 1% BSA in 1×PBS for 30 min. The mats were then incubated in 1×PBS with the TRITC-conjugated phalloidin for 1 h. After rinsing with the wash buffer three times, mats were dipped face down onto a glass slide with a drop of Prolong Gold anti-fade mounting media with DAPI (Invitrogen). Cells were imaged on an inverted microscope equipped with FITC, TRITC, and DAPI filter cube sets. For this experiment 3 replicates of each condition were used.

Cell Culture Stability Assay.

Coatings patterned with cRGDfK or cRGDfC or the non-adhesive cRADfC or cRADfK on 2 mm diameter spots were sterilized by incubating in 70% ethanol for 20 minutes, which was followed by two rinses with sterile PBS. Coatings were then incubated at 37° C. in αMEM+10% FBS or PBS for 2 weeks. Media was replaced every 3-4 days. After 2 weeks, the samples were rinsed with sterile PBS and deionized water, then hMSCs were seeded at 10,000 cells/$cm^2$ and let adhere for 6-7 hours before fixing and staining for actin and nuclei.

Passage of hMSCs.

Plastic polystyrene dishes (round, Fisher Scientific) with area of 150 $cm^2$ or 70 $cm^2$ were coated with a 30 nm polymer coating, as previously described, and crosslinked at 85° C. The cRGDfK peptide was coupled to approximately half of the dish, using a PDMS strip as a divider. The peptide was coupled at 0.084 mM concentration in the 1.5 M Sodium Sulfate buffer at pH 9.5 for 1 hour at room temperature. The dish was then soaked in PBS for 30 minutes, followed by 70% ethanol for 20 minutes to sterilize. hMSCs (P6) were seeded at low density 1,000 cells/$cm^2$ in αMEM+10% FBS. Cells reached confluence in 3 days. Versene solution (Life Technologies) was warmed to 37° C. in a water bath. Media above the cells was aspirated and rinsed twice with PBS before placing 10 mL of Versene solution into the dish for 1.5 minutes. Versene was then aspirated and fresh αMEM (5 mL three times) was used to remove the cells from the surface. On the same surface, 20% of the cells were reseeded down and imaged after 24 hours.

H1 Pluripotent Stem Cell Culture.

H1 human ESCs (WiCell) were maintained on 6-well plates coated with Matrigel (8.7 µg/$cm^2$; BD Biosciences) in Essential 8 medium (E8; Invitrogen) with daily media exchange, and passaged using Versene (Invitrogen) every 3 to 4 days. For substrate seeding studies, cells were washed with PBS and incubated with TrypLE (Invitrogen) at 37° C. for 5 minutes to promote singularization. Cell suspensions were diluted with E8 supplemented with 5 µM Rho kinase inhibitor (Y-27632; CalBiochem) and pelleted by centrifugation at 200 g for 5 minutes before counting by hemacytometer and seeding at $1.8 \times 10^5$ cells/$cm^2$.

Statistical Analysis.

Values reported are the mean plus or minus the standard deviation. Experiments were analyzed using a two-tailed Student's t-test. Data were considered "statistically significant" if $p<0.05$.

Example 2

This example illustrates a P(VDM-r-GMA) polymer coating that incorporates VDM chemistry for use as a template for stem cell growth and expansion.

Copolymers VDM-r-GMA were synthesized by atomic transfer radical polymerization (ATRP) with a 200 to 1 monomer to initiator ratio. Briefly, VDM (9.0 mmol, 2.5 g) and GMA (0.5 mmol, 0.28 g) were added to a Schlenk flask with copper (I) bromide (0.05 mmol, 21.4 mg), N,N,N',N",N"-pentamethyldiethylenetriamine (PMDETA, 0.05 mmol, 26 mg) and 3 mL toluene. The flask was degassed by three freeze-pump-thaw cycles. The flask was then heated to 60° C. in an oil bath, and the initiator ethyl-2-bromoisobyrate (0.05 mmol, 29.3 mg) was injected to start the reaction. The reaction was allowed to proceed for 4.5 hours, after which the copolymer was precipitated in hexane and dried. $H^1$ NMR characterization showed the composition to be 11.9 mol. % GMA and 88.1 mol. % VDM. Gel permeation chromatography gave a number average molecular weight of 10,815 Da and a dispersity of 1.2. The VDM-r-GMA copolymer is not soluble in water or ethanol mixtures, limiting its applicability to plastic substrates. Therefore, the copolymer was spin coated from cyclopentanone (12 mg/ml) onto glass substrates and crosslinked at 160° C. for 6 hours. The copolymer VDM-r-GMA was modified with functional amines after crosslinking. Unmodified films promoted adhesion and spreading of hMSCs in cell culture medium with 10% fetal bovine serum. To inhibit adhesion, a 660 µM solution of methoxypolyethylene glycol amine 750 (Sigma Aldrich) in deionized water was applied for 1 hour. hMSCs were seeded at 5,000 cells/$cm^2$ at passage 7 and allowed to adhere for 6 hours, after which they were imaged. Unmodified (blank) areas of the coating readily promoted cell adhesion, which was non-specific in nature. The region that was modified with PEG-amine resisted cell adhesion.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A random copolymer of glycidyl methacrylate and 4,4-dimethyl-2-vinylazlactone comprising the structure:

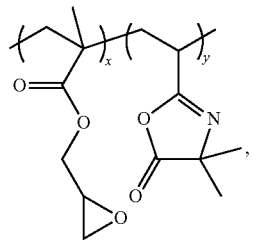

wherein x and y represent the mole fractions of the polymerized glycidyl methacrylate and 4,4-dimethyl-2-vinylazlactone monomers; the glycidyl groups and the azlactone groups are distributed randomly along the copolymer backbone; the random copolymer comprises no greater than about 30 mole percent of additional monomer; and the copolymer comprises from about 1 to about 15 mole percent polymerized glycidyl methacrylate monomer and from about 99 to about 85 mole percent polymerized 4,4-dimethyl-2-vinylazlactone monomer.

2. The copolymer of claim 1, comprising from 1 to 15 mole percent polymerized glycidyl methacrylate monomer and from 99 to 85 mole percent polymerized 4,4-dimethyl-2-vinylazlactone monomer.

3. The copolymer of claim 1 consisting of polymerized glycidyl methacrylate and 4,4-dimethyl-2-vinylazlactone monomer.

4. The copolymer of claim 1, comprising no greater than 10 mole percent additional monomer.

5. The copolymer of claim 1, comprising no greater than 5 mole percent additional monomer.

6. The copolymer of claim 1, wherein the copolymer is free of polyethylene glycol monomers polymerized into the copolymer backbone chain.

7. The copolymer of claim 1, comprising from 2 to 12 mole percent of the polymerized glycidyl methacrylate monomer.

8. A coated substrate comprising:
a substrate having a surface; and
a film of crosslinked random copolymers on the surface of the substrate, the crosslinked random copolymers having backbone chains comprising polymerized 4,4-dimethyl-2-vinylazlactone monomers and monomers that provide covalent crosslinks between the backbone chains, the crosslinked random copolymers comprising the structure:

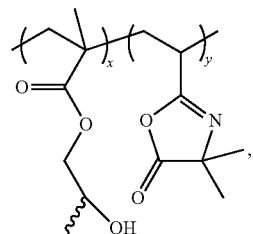

wherein x and y represent the mole fractions of the crosslinked monomer and the 4,4-dimethyl-2-vinylazlactone monomers; ⁄ represents a crosslink to another copolymer backbone chain; and the glycidyl groups, the crosslinks, and the azlactone groups are distributed randomly along the copolymer backbone.

9. The coated substrate of claim 8, comprising no greater than about 30 mole percent of additional monomer.

10. The coated substrate of claim 9, wherein the crosslinked random copolymers comprise from about 1 to about 15 mole percent of the monomers that provide covalent crosslinks between the backbone chains and from about 99 to about 85 mole percent of the polymerized 4,4-dimethyl-2-vinylazlactone monomer.

11. The coated substrate of claim 9, wherein the film of crosslinked random copolymers has a thickness of no greater than 100 nm.

12. The coated substrate of claim 11, wherein the film of crosslinked random copolymers has a thickness in the range from 5 nm to 50 nm.

13. The coated substrate of claim 11, wherein the film of crosslinked random copolymers is not covalently bound to the surface of the substrate.

14. The coated substrate of claim 13, wherein the film of crosslinked random copolymers is characterized in that it will not delaminate from the substrate in deionized water for a period of at least 30 days or degrade in deionized water for a period of at least 30 days.

15. The coated substrate of claim 9, wherein the random copolymers of the film of crosslinked random copolymers comprise pendant epoxy functionalities.

16. A random copolymer of glycidyl methacrylate, 4,4-dimethyl-2-vinylazlactone, and additional polymerized monomer, the random copolymer comprising the structure:

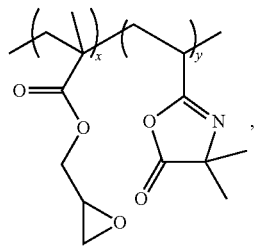

wherein x and y represent the mole fractions of the polymerized glycidyl methacrylate and 4,4-dimethyl-2-vinylazlactone monomers; the glycidyl groups and the azlactone groups are distributed randomly along the copolymer backbone; and the random copolymer comprises no greater than about 30 mole percent of the additional polymerized monomer, wherein the additional polymerized monomers comprise polymerized hydroxyethyl methacrylate monomer, polymerized methyl methacrylate monomer, or poly(vinyl alcohol).

* * * * *